(12) United States Patent
Ha et al.

(10) Patent No.: US 11,479,878 B2
(45) Date of Patent: Oct. 25, 2022

(54) METHODS FOR GENOME CHARACTERIZATION

(71) Applicants: DANA-FARBER CANCER INSTITUTE, INC., Boston, MA (US); THE BROAD INSTITUTE, INC., Cambridge, MA (US); PRESIDENT AND FELLOWS OF HARVARD COLLEGE, Cambridge, MA (US)

(72) Inventors: Gavin Ha, Boston, MA (US); Viktor Adalsteinsson, Cambridge, MA (US); Samuel Freeman, Cambridge, MA (US)

(73) Assignees: DANA-FARBER CANCER INSTITUTE, INC., Boston, MA (US); THE BROAD INSTITUTE, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 301 days.

(21) Appl. No.: 16/084,890

(22) PCT Filed: Mar. 16, 2017

(86) PCT No.: PCT/US2017/022792
§ 371 (c)(1),
(2) Date: Sep. 13, 2018

(87) PCT Pub. No.: WO2017/161175
PCT Pub. Date: Sep. 21, 2017

(65) Prior Publication Data
US 2019/0078232 A1    Mar. 14, 2019

Related U.S. Application Data

(60) Provisional application No. 62/359,544, filed on Jul. 7, 2016, provisional application No. 62/309,299, filed on Mar. 16, 2016.

(51) Int. Cl.
*C12Q 1/6886* (2018.01)
*C12Q 1/6869* (2018.01)
(Continued)

(52) U.S. Cl.
CPC ............ *C40B 40/08* (2013.01); *C12Q 1/68* (2013.01); *C12Q 1/6806* (2013.01); *C12Q 1/686* (2013.01);
(Continued)

(58) Field of Classification Search
CPC ... C12Q 1/6869; C12Q 1/6886; C12Q 1/6827
See application file for complete search history.

(56) References Cited

U.S. PATENT DOCUMENTS 9,205,098 B2    12/2015   Tidmarsh
2016/0053301 A1    2/2016   Raymond et al.

FOREIGN PATENT DOCUMENTS

WO    2014014497 A1    1/2014
WO    2014039556 A1    3/2014
(Continued)

OTHER PUBLICATIONS

Small, E.J. et al. Molecular Therapy 14(1):107 (Jul. 2006). (Year: 2006).*

(Continued)

*Primary Examiner* — Diana B Johannsen
(74) *Attorney, Agent, or Firm* — Melissa Hunter-Ensor; Nicholas R. Bailor; Greenberg Traurig, LLP

(57) ABSTRACT

The invention provides methods of using low coverage sequencing to assess the relative fraction of tumor versus normal DNA in a sample, and to assess copy number alterations present in the sample.

20 Claims, 25 Drawing Sheets

(51) Int. Cl.
  *C40B 40/08*  (2006.01)
  *C12Q 1/68*  (2018.01)
  *C12Q 1/6806*  (2018.01)
  *C12Q 1/686*  (2018.01)
  *C12Q 1/6827*  (2018.01)

(52) U.S. Cl.
  CPC ......... *C12Q 1/6869* (2013.01); *C12Q 1/6886* (2013.01); *C12Q 1/6827* (2013.01); *C12Q 2600/112* (2013.01); *C12Q 2600/156* (2013.01); *C12Q 2600/16* (2013.01)

(56) References Cited

FOREIGN PATENT DOCUMENTS

| WO | 2014151117 A1 | 9/2014 |
| WO | 2015100427 A1 | 7/2015 |
| WO | 2015137870 A1 | 9/2015 |
| WO | 2016028316 A1 | 2/2016 |

OTHER PUBLICATIONS

Kozarewa, I., Turner D.J. (2011) Chapter 18 of "High-Throughput Next Generation Sequencing. Methods in Molecular Biology", vol. 733, Kwon Y., Rieke S. (eds), Humana Press, Totowa, NJ. (online Feb. 23, 2011). (Year: 2011).*

Raley, C. et al. bioRxiv preprint, doi.org//10.1101/003566, pp. 1-13 (Mar. 25, 2014). (Year: 2014).*

Heitzer et al., "Tumor-associated copy number changes in the circulation of patients with prostate cancer identified through whole-genome sequencing," Genome Medicine, Apr. 5, 2013 (Apr. 5, 2013); vol. 5, No. 4, pp. 30-45, (16 pages).

Klambauer et al., "cn.MOPS: mixture of Poissons for discovering copy number variations in next-generation sequencing data with a low false discovery rate," Nucleic Acids Research, Feb. 1, 2012 (Feb. 1, 2012); vol. 40, No. 9, e69, doi:10.1093/nar/gks003, (14 pages).

Sims et al., "Sequencing depth and coverage: key considerations in genomic analyses," Nature Reviews Genetics, Feb. 2014; vol. 15, No. 2, pp. 121-132; doi:10.1038/nrg3642, (12 pages).

Xie Chao et al., "CNV-seq, a new method to detect copy number variation using high-throughout sequencing," BMC Bioinformatics, Biomed Central, London, GB, Mar. 6, 2009 (Mar. 6, 2009); vol. 10:80; doi:10.1186/1471-2105-10-80, (9 pages).

Zhenhua Yu et al., "CLImAT: accurate detection of a copy number alteration and loss of heterozygosity in impure and aneuploid tumor samples using whole-genome sequencing data," Bioinformatics, 2014, vol. 30, No. 18, pp. 2576-2583; advance access publication: May 19, 2014, (8 pages).

Extended European Search Report in corresponding European Patent Application No. 17767566.7, dated Oct. 24, 2019 (11 pages).

International Search Report and Written Opinion for corresponding PCT Patent Application No. PCT/US17/22792, dated Jun. 16, 2017 (15 pages).

Dago, AE et al., "Rapid Phelotypic and Genomic Change in Response to Therapeutic Pressure in Prostate Cancer Inferred by High Content Analysis of Single Circulating Tumor Cells," PLOS One, Aug. 1, 2014, vol. 9, Issue 8, e101777.

Kreuzinger, C. et al., "Molecular characterization of 7 new established cell lines from high grade serous ovarian cancer," Cancer Letters, 2015, vol. 362, pp. 218-288.

Lonigro, RJ. et al., "Detection of Somatic Copy Number Alterations in Cancer Using Targeted Exome Capture Sequencing," NEOPLASIA, Nov. 2011, vol. 13, No. 11, pp. 1019-1025.

Scheinin, I. et al., "DNA copy Number analysis of fresh and formalin-fixed specimens by shallow whole-genome sequencing with identification and exclusion of problematic regions in the genome assembly," Genome Research, 2014, vol. 24, pp. 2022-2032.

Carter et al. "Absolute quantification of somatic DNA alterations in human cancer," Nature Biotechnology, May 2012, vol. 30, No. 5, pp. 413-421.

Ha et al., "Integrative analysis of genome-wide loss of heterozygosity and monoallelic expression at nucleotide resolution reveals disrupted pathways in triple-negative breast cancer," Genome Research, 2012, vol. 22, pp. 1995-2007.

Ha et al., "TITAN: inference of copy number architectures in clonal cell populations from tumor whole-genome sequence data," Genome Research, 2014, vol. 24, pp. 1881-1893.

Klevebring et al., "Evaluation of Exome Sequencing to Estimate Tumor Burden in Plasma," PLoS One, Aug. 2014, vol. 9, No. 8, e104417, pp. 1-10.

Lawrence et al., "Discovery and saturation analysis of cancer genes across 21 tumor types," Nature, Jan. 23, 2014, vol. 505, No. 7484, pp. 495-501.

Lawrence et al., "Mutational heterogeneity in cancer and the search for new cancer genes," Nature, Jul. 11, 2013, vol. 499, No. 7457, pp. 214-218.

Magi et al., "Read count approach for DNA copy number variants detection," Bioinformatics, 2012, vol. 28, No. 4, pp. 470-478.

Mateo et al., "DNA-Repair Defects and Olaparib in Metastatic Prostate Cancer," The New England Journal of Medicine, Oct. 29, 2015, vol. 373, No. 18, pp. 1697-1708.

Rizvi et al., "Mutational landscape determines sensitivity to PD-1 blockade in non-small cell lung cancer," Science, Apr. 3, 2015, vol. 348, No. 6230, pp. 124-128.

Van Loo et al., "Allele-specific copy number analysis of tumors," Proceedings of the National Academy of Sciences of the United States of America, Sep. 28, 2010, vol. 107, No. 39, pp. 16910-16915.

Yau et al., "A statistical approach for detecting genomic aberrations in heterogeneous tumor samples from single nucleotide polymorphism genotyping data," Genome Biology, 2010, vol. 11, No. R92, pp. 1-15.

Office Action dated Sep. 15, 2021 in corresponding European Patent Application No. 17767566.7 (9 pages).

* cited by examiner

1) Cell-free DNA library construction

2) Ultra low-pass whole-genome sequencing (0.1x)

3) Whole-exome sequencing

Application to large cohorts

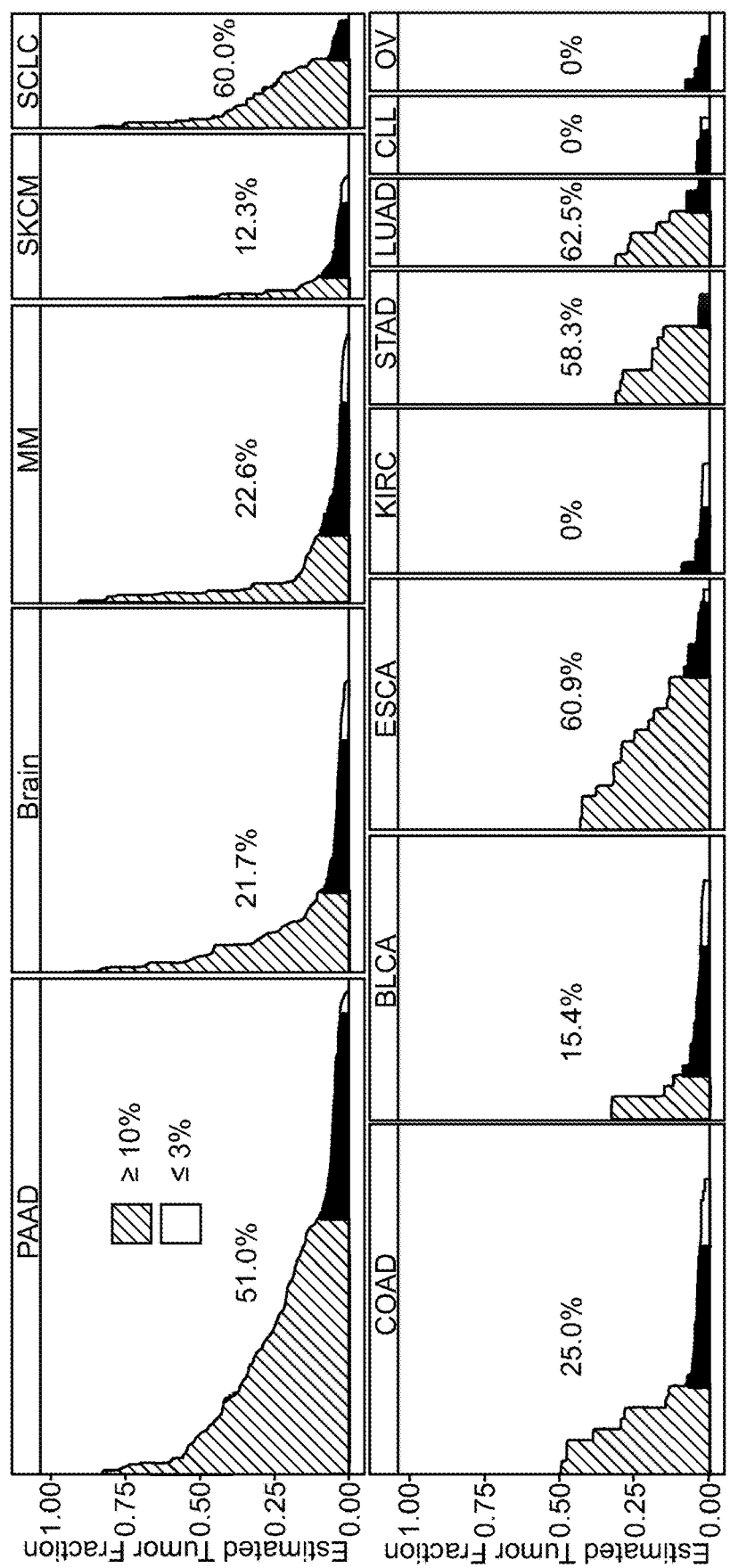

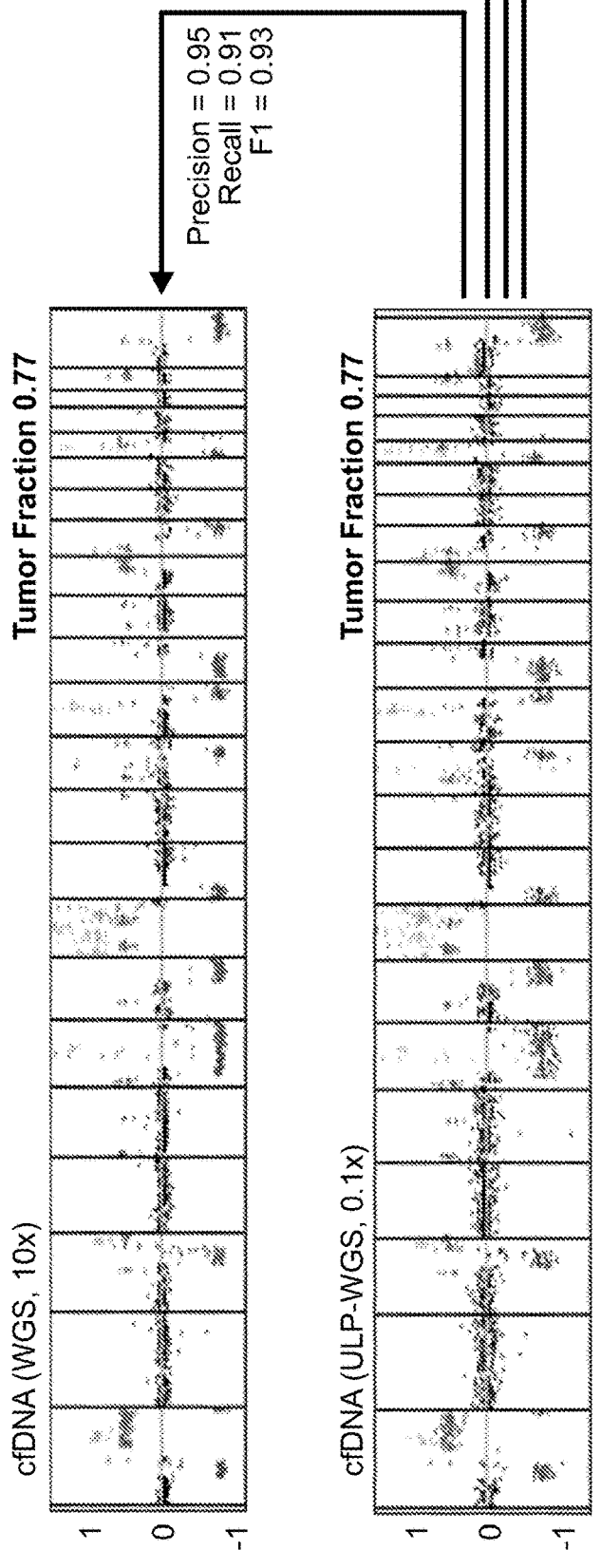

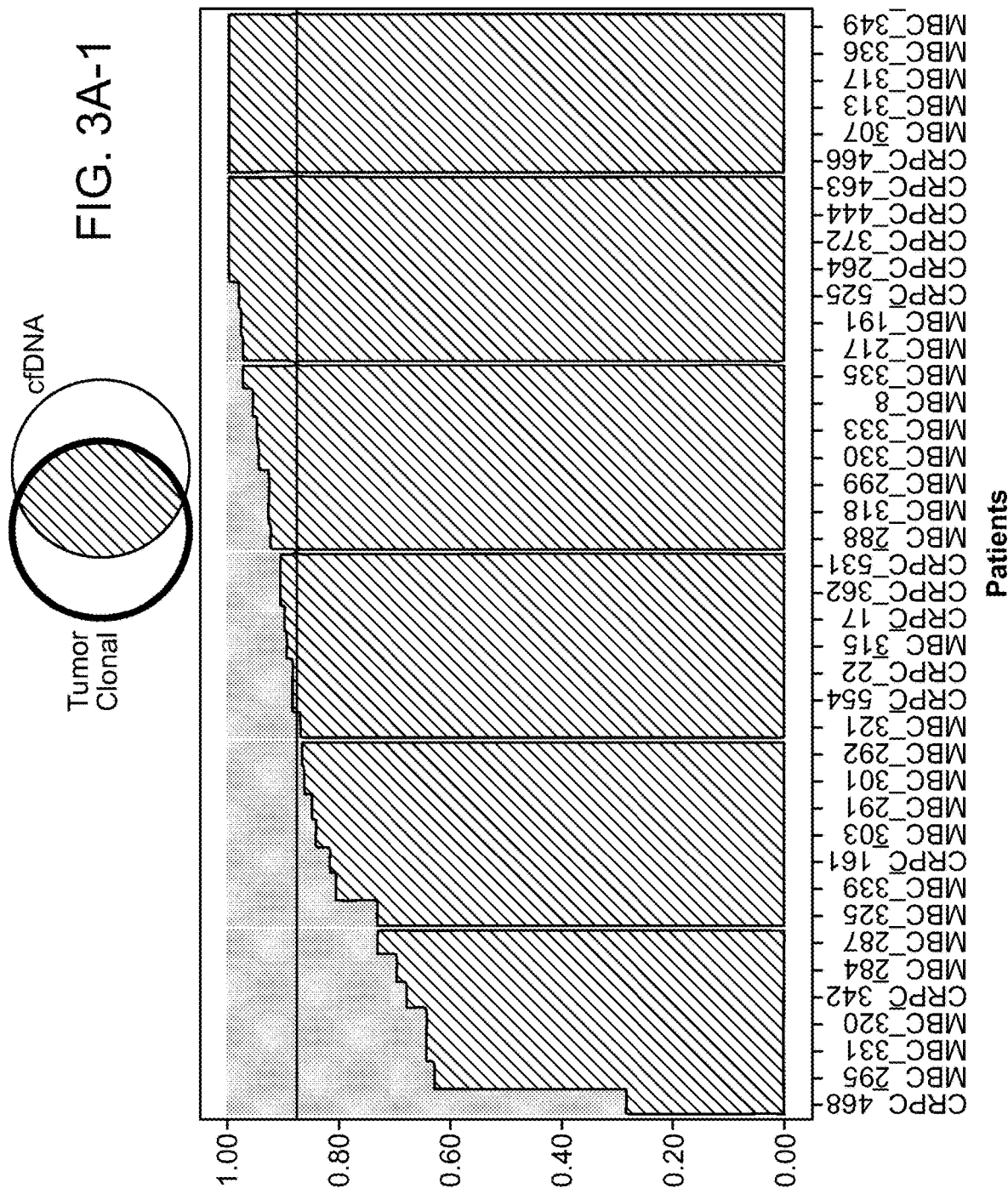

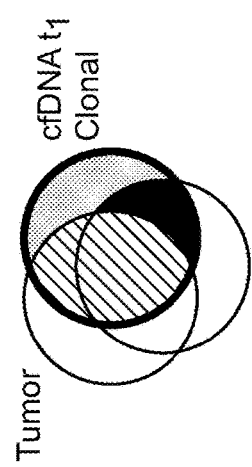
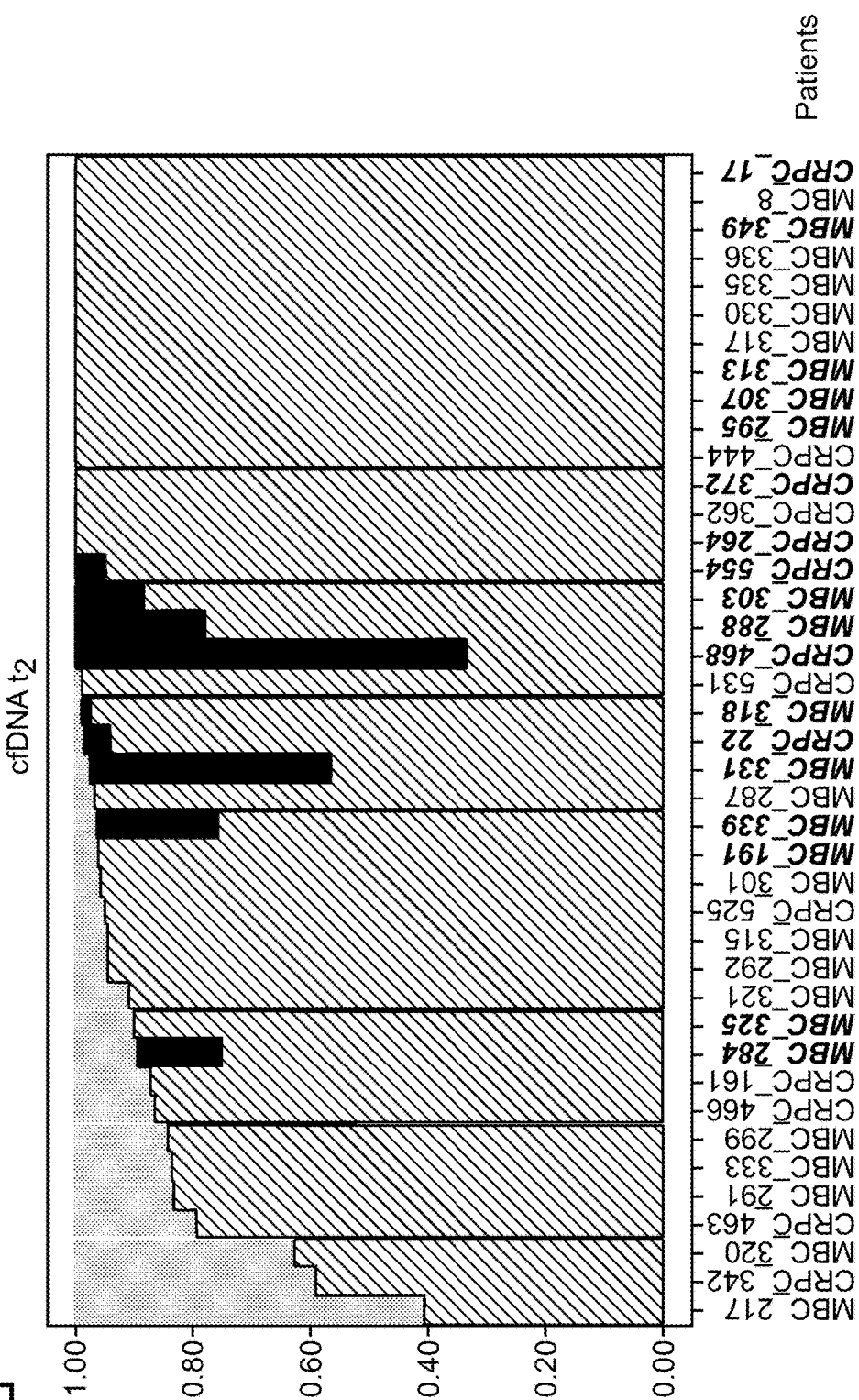
FIG. 3B
FIG. 3B-1
| FIG. 3B-1 |
| FIG. 3B-2 |

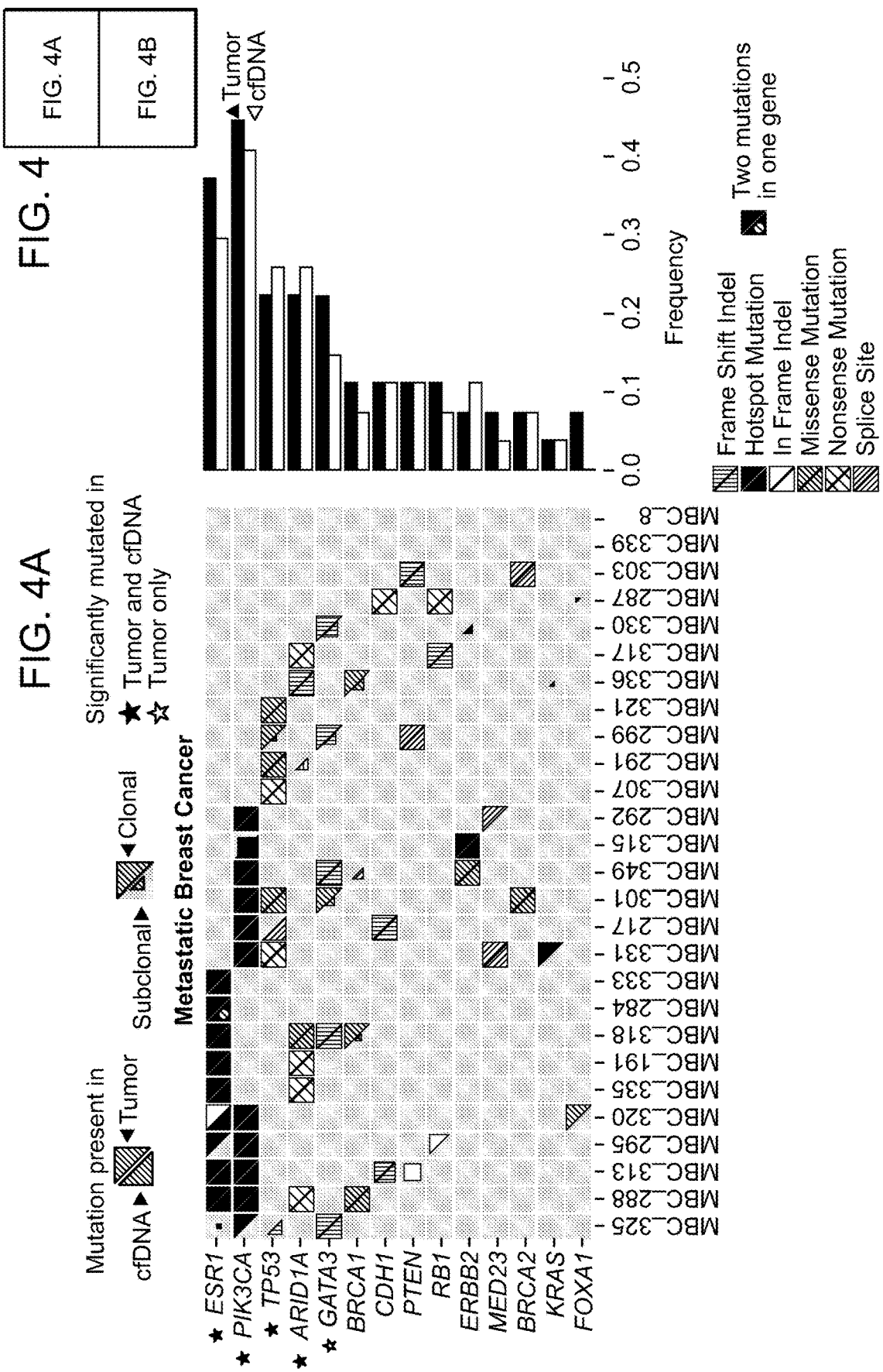

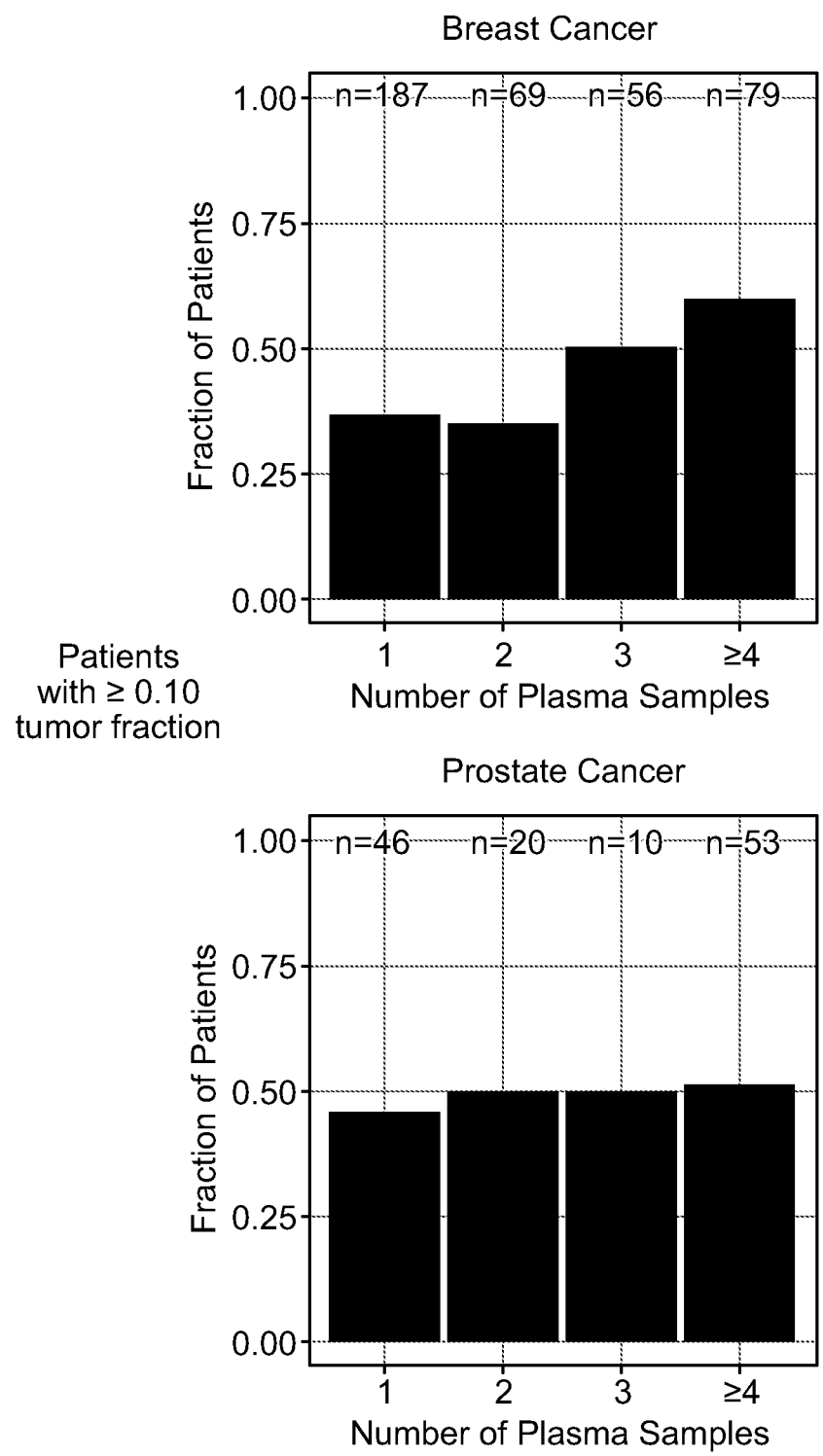

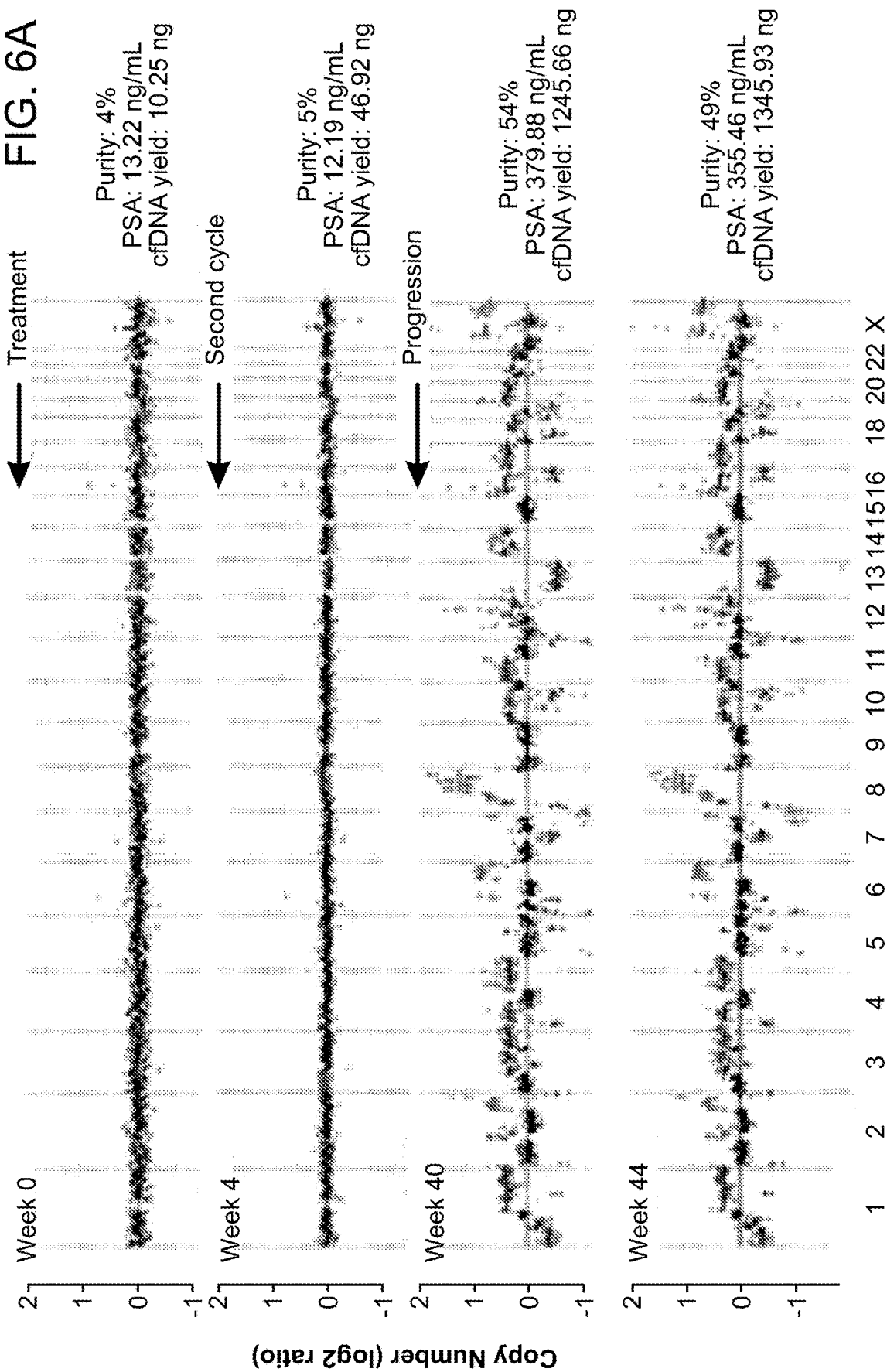

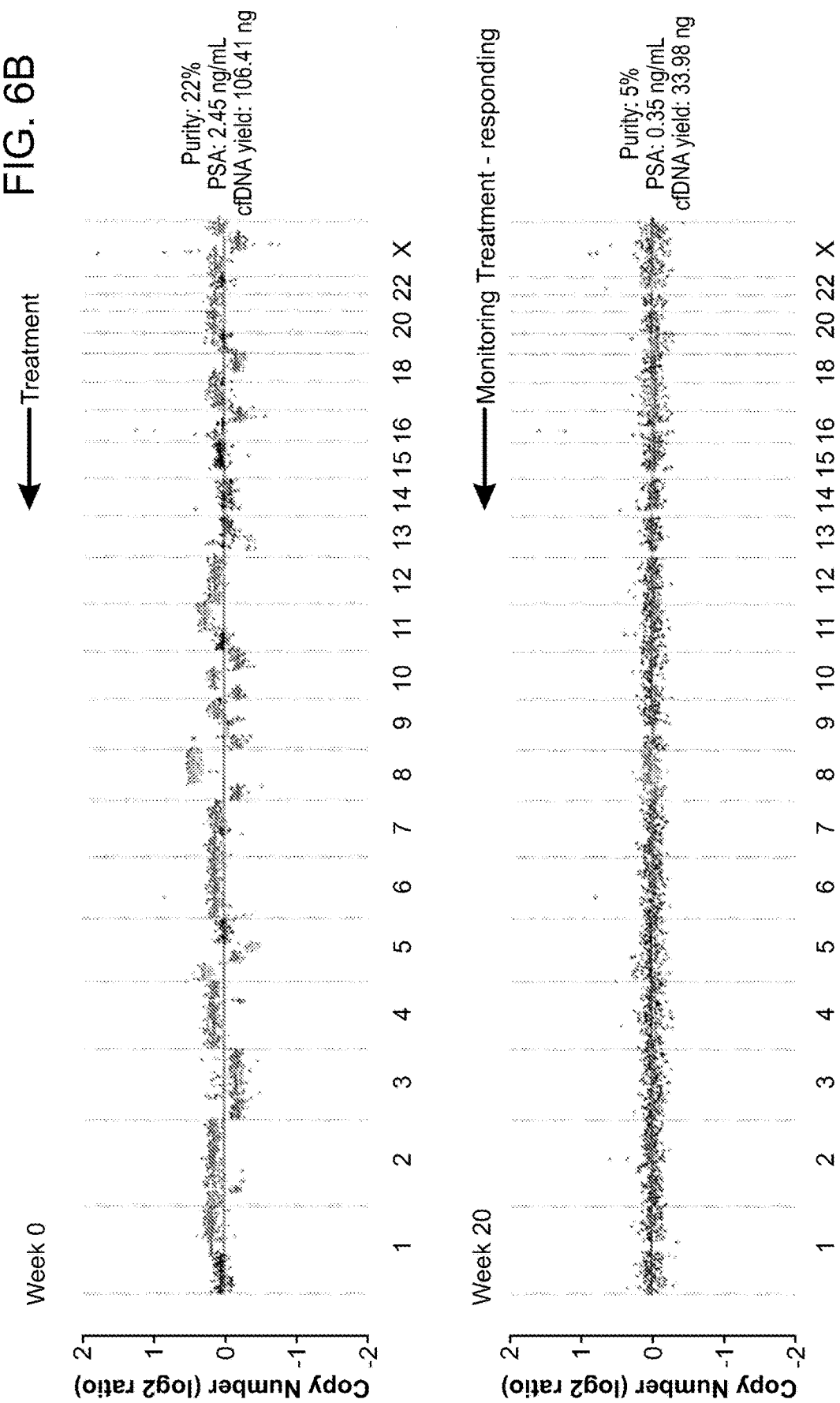

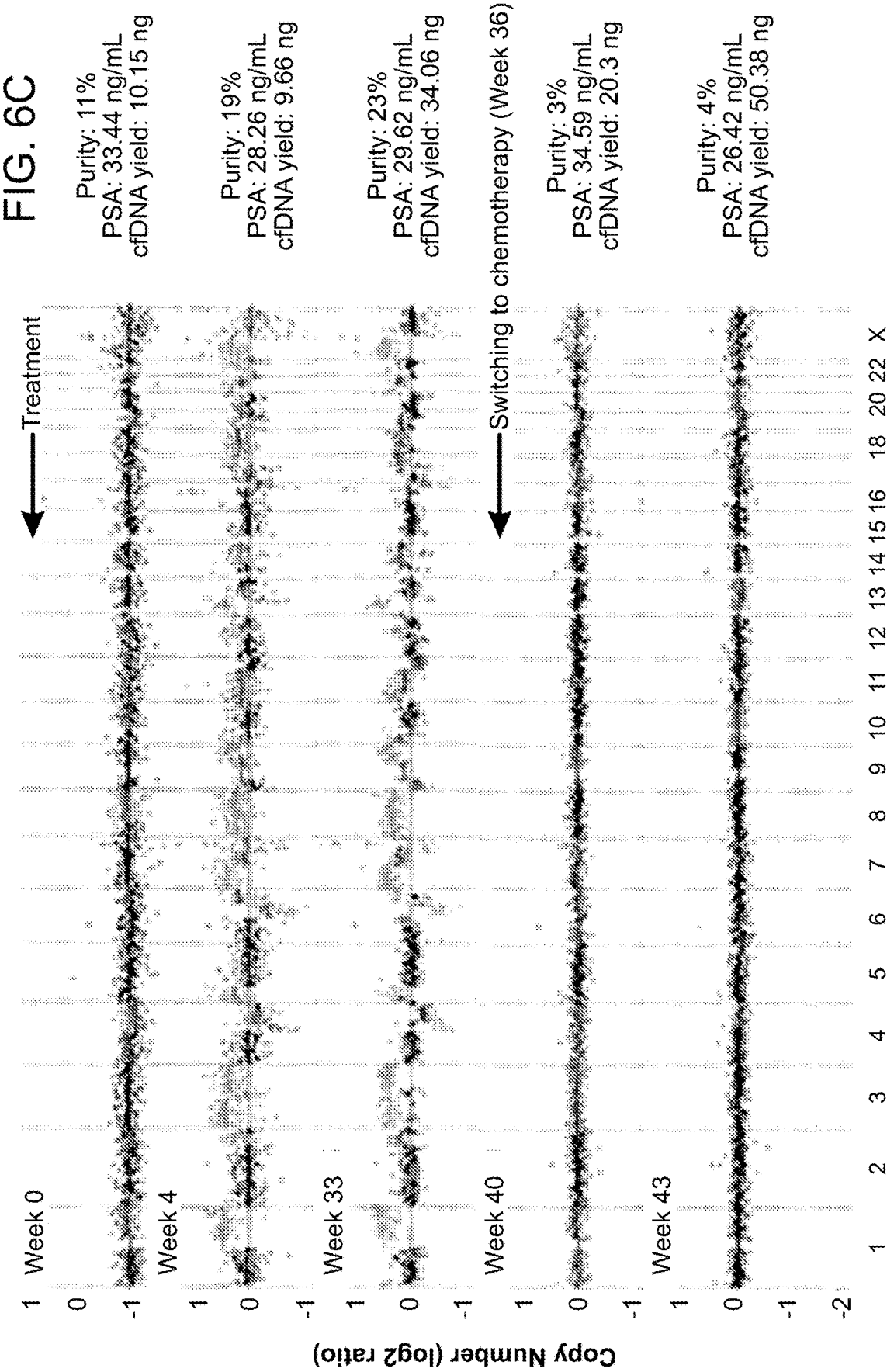

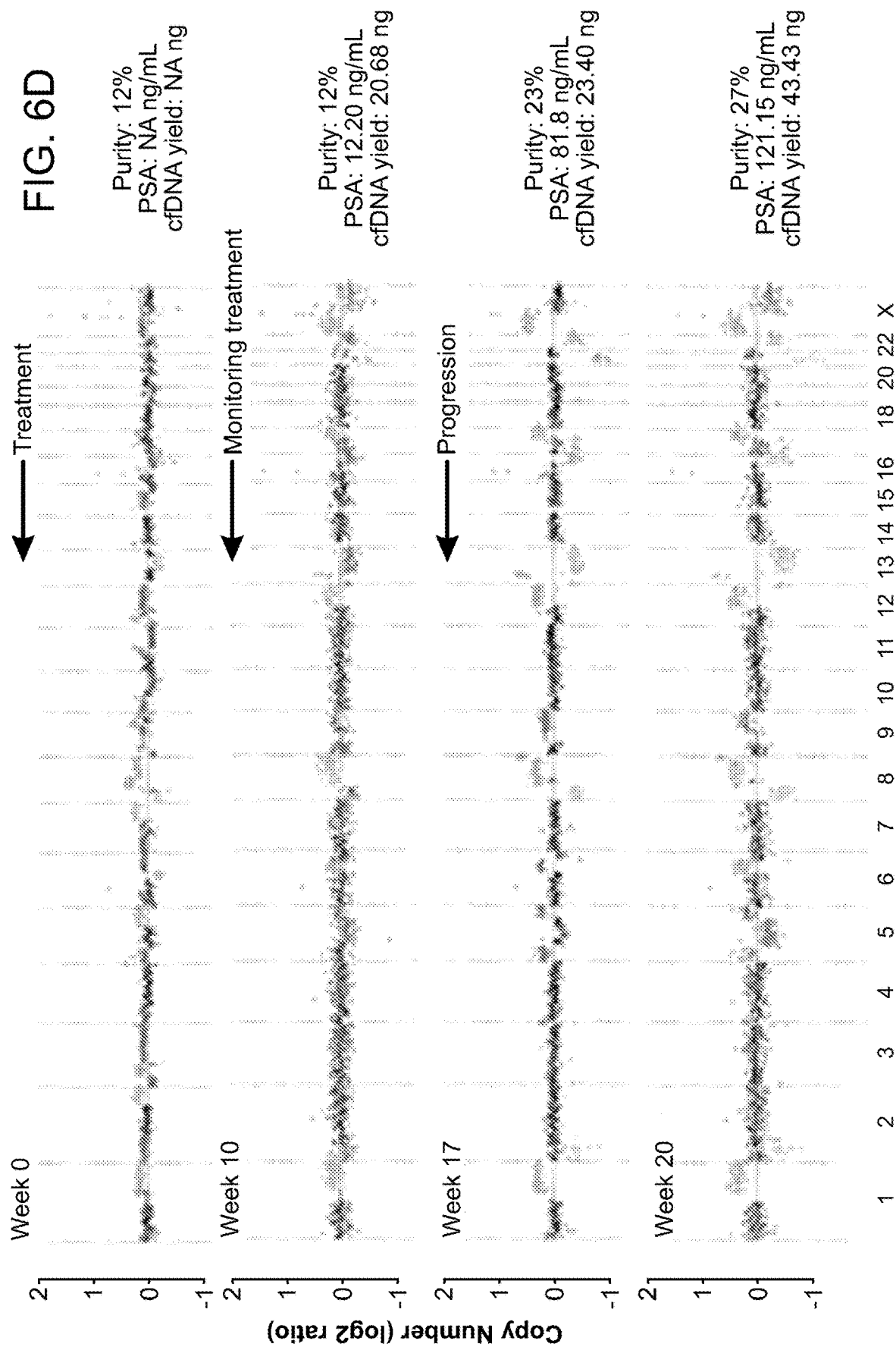

METHODS FOR GENOME CHARACTERIZATION

CROSS-REFERENCE TO RELATED APPLICATIONS

This application is the U.S. national phase application, pursuant to 35 U.S.C. § 371, of PCT International Application Ser. No.: PCT/US2017/022792, filed Mar. 16, 2017, designating the United States and published in English, which claims priority to and the benefit of U.S. Provisional Application Nos. 62/309,299 and 62/359,544, filed Mar. 16, 2016 and Jul. 7, 2016, respectively, the disclosures of each of which are incorporated herein by reference in their entirety.

BACKGROUND OF THE INVENTION

Comprehensive genomic characterization of metastatic cancer stands to uncover novel alterations of clinical significance. A major challenge is that metastatic tumors are infrequently biopsied. Cell-free DNA is shed abundantly into the bloodstream from metastatic tumors, presenting an opportunity for genomic discovery in settings where tumor biopsies are least accessible. Conventional methods for characterizing cancers rely on the sequencing of particular genes, such as BRCA1, BRCA2, and p53, where the presence of mutations is associated with uncontrolled cell proliferation. This approach only interrogates genes previously shown to be associated with cancer. It fails to identify genes that have not yet been shown to be dysregulated in cancer. The advent of next-generation shot gun sequencing provides researchers with the ability to rapidly sequence a whole genome and then use bioinformatics-based approaches to analyze the data. These approaches have made possible the characterization of whole cancer genomes and the discovery of alterations in chromosomal structure, such as amplifications, deletions, translocations, and inversions. Next-generation shotgun sequencing typically requires sequencing every base in a sample several times to reliably determine the base call. Researchers determine the necessary coverage level (i.e., number of times the genome must be sequenced) based on the type of study, gene expression level, size of reference genome, published literature, and best practices defined by the scientific community. Most publications require between 10× to 30× depth of coverage for the detection of human genome mutations/SNPs/rearrangements depending on the application and statistical model. A standard whole-genome analysis often requires 30-60× coverage. For ChIP-Seq studies where reads map to only a subset of a genome, publications often require coverage around 100×. This level of sequencing coverage is expensive and time consuming. Accordingly, improved methods for characterizing cancer are urgently required.

SUMMARY OF THE INVENTION

As described herein below, the present invention provides methods of using low coverage sequencing to assess the relative fraction of tumor versus normal DNA in a sample, and to assess copy number alterations present in the sample. This approach can be used, for example, to qualify samples for whole exome sequencing, for diagnosis of cancer or other disease states, and to monitor cancer therapy.

In one aspect, the invention features a method of characterizing DNA in a biological sample containing or suspected of containing tumor-derived DNA, the method involving isolating fragments of DNA from a biological sample; constructing a library containing the fragments; sequencing the library to about 0.01-5× genome or exome wide sequencing coverage; and detecting chromosomal copy number alterations in the sequence, where detection of chromosomal copy number alterations indicates that at least a portion of the DNA in the sample was derived from a neoplastic cell and failure to detect such alterations indicates that cell free DNA present in the sample is not derived from a neoplastic cell.

In another aspect, the invention features a method of characterizing DNA in a biological sample, the method involving isolating fragments of cell free DNA from a biological sample; constructing a library containing the fragments; sequencing the library to about 0.1× genome or exome-wide sequencing coverage; and detecting chromosomal copy number alterations in the sequence.

In another aspect, the invention features a method of characterizing DNA in a biological sample, the method involving isolating fragments of DNA from a biological sample; constructing a library containing the fragments; sequencing the library to at least about 0.01-5× genome or exome-wide sequencing coverage; and detecting focal chromosomal copy number alterations in the sequence.

In another aspect, the invention features a method of determining the purity of DNA in a sample, the method involving isolating fragments of DNA from a biological sample; constructing a library containing the fragments; sequencing the library to at least about 0.1× genome or exome-wide sequencing coverage; detecting chromosomal copy number alterations in the sequence; and analyzing the chromosomal copy number alterations present in the sample to determine the percentage of DNA that is derived from a tumor cell.

In another aspect, the invention features a method of identifying a subject as having a neoplasia, the method involving isolating fragments of cell free DNA from a biological sample derived from the subject; constructing a library containing the fragments; sequencing the library to at least about 0.01-5× exome or genome-wide sequencing coverage; and detecting the presence or absence of chromosomal copy number alterations in the sequence, where the presence of chromosomal copy number alterations identifies the subject as having a neoplasia, and the absence of chromosomal copy number alterations indicates that no neoplasia was detected in the sample from the subject.

In another aspect, the invention features a method of monitoring the disease state of a subject, the method involving isolating fragments of cell free DNA from two or more biological samples, where the first biological sample is obtained at a first time point and a second or subsequent biological sample is obtained at a later time point; constructing two or more libraries each containing fragments from the samples; sequencing the libraries to at least about 0.01-5× exome or genome-wide sequencing coverage; and comparing the chromosomal copy number alterations in the sequence over time, thereby monitoring the disease state of the subject. In one embodiment, an increase in chromosomal copy number alterations between a first time point and a later time point indicates that the subject's disease state has progressed. In another embodiment, a decrease in chromosomal copy number alterations between a first time point and a later time point indicates that the subject's disease state has stabilized or is not progressing. In another embodiment, the first time point is prior to treatment. In another embodiment, the second or subsequent time point is during the course of treatment. In another embodiment, the disease state is a cancer that is any one of prostate cancer, metastatic prostate cancer, breast cancer, triple negative breast cancer, lung cancer, and colon cancer.

In another aspect, the invention provides a method of characterizing the efficacy of treatment of a subject having a disease characterized by an increase in chromosomal copy number, the method involving isolating fragments of cell free DNA from two or more biological samples derived from a subject undergoing cancer therapy, where the first biological sample is obtained at a first time point and a second or subsequent biological sample is obtained at a later time point; constructing two or more libraries each containing fragments from the samples; sequencing the libraries to at least about 0.01-5× genome or exome-wide sequencing coverage; and comparing the focal chromosomal copy number alterations in the sequence over time, thereby characterizing the efficacy of treatment. In one embodiment, a decrease in chromosomal copy number alterations between the first and second time points indicate that the treatment is effective. In another embodiment, a decrease in chromosomal copy number alterations between the first and second time points indicate that the treatment lacks efficacy. In another embodiment, a decrease in chromosomal copy number alterations between the first and second time points indicates that the disease has acquired resistance to the treatment. In another embodiment, the disease is cancer. In another embodiment, the treatment is an anti-cancer therapy that is chemotherapy, radiotherapy, or surgery. In another embodiment, samples are collected at 5, 15, or 30 minute intervals while a cancer therapy is administered. In another embodiment, samples are collected at 3, 6, 9, 12, 24, 36, or 72 hour intervals. In another embodiment, samples are collected at 1, 2, 3, 4, 5, or 6 week intervals.

In various embodiments of any of the above aspects or any other aspect of the invention delineated herein, the DNA is cell free DNA. In other embodiments, the exome wide or genome wide sequencing coverage is any one or more of 0.01, 0.05, 0.1, 0.5, 1, 2, 3, 4, and 5×. In various embodiments, detection of an alteration in copy number at the focal point identifies the presence of tumor derived cell free DNA present in the sample. In other embodiments, failure to detect an alteration in copy number indicates the absence of tumor derived cell free DNA present in the sample. In other embodiments, sequence coverage correlates with the purity of tumor derived DNA (also termed "tumor fraction"), such that the sequence coverage is about 0.01-5× when the purity is about 50%. In other embodiments, sequence coverage correlates with the purity of tumor derived DNA, such that the sequence coverage is about 0.05-5× when the purity is about 25%. In other embodiments, sequence coverage correlates with the purity of tumor derived DNA, such that the sequence coverage is about 0.005-5× when the purity is about 75%. In other embodiments, the focal copy number alteration correlates with at least about 3% purity of tumor derived DNA. In other embodiments, the sequencing is whole genome sequencing. In other embodiments, the focal copy number alteration is between about 1 KB and 100 MB (e.g., of about 1 KB, 3 KB, 5 KB, 10 kb, 50 kb, 100 kb, 500 kb, 2 MB, 3 MB, 4 MB, 5 MB, 10 MB, 50 MB, or 100 MB of DNA). In still other embodiments, the biological sample is a tissue sample or a liquid biological sample that is blood, plasma, serum, cerebrospinal fluid, phlegm, saliva, urine, semen, prostate fluid, breast milk, and/or tears. In still other embodiments, the sample is derived from a subject having or suspected of having a neoplasia. In still other embodiments, the sample is a fresh or archival sample derived from a subject having a cancer that is prostate cancer, metastatic prostate cancer, breast cancer, triple negative breast cancer, lung cancer, colon cancer, or any other cancer containing aneuploid cells. In still other embodiments, the cancer is metastatic castration resistant prostate cancer or metastatic breast cancer. In still other embodiments, the patient is being treated for a neoplasia. In still other embodiments, the method is used to screen or otherwise qualify the sample prior to whole exome sequencing or prior to generating a cell line from the sample. In still other embodiments, the method further involves carrying out whole exome sequencing. In still other embodiments, the method is used to qualify the sample prior to producing a cell line from the sample. In various embodiments, the sequencing or ultra low pass-whole genome sequencing is performed by bisulfite sequencing (e.g., ultra low pass-whole genome bisulfite sequencing (ULP-WGBS)).

Other features and advantages of this invention will be apparent from the detailed description, and from the claims.

Definitions

Unless defined otherwise, all technical and scientific terms used herein have the meaning commonly understood by a person of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "aneuploidy" is meant in the context of a cell having an abnormal number of chromosomes relative to a cell of normal ploidy.

"Tumor derived DNA" means DNA that is derived from a cancer cell rather than a healthy control cell. Tumor derived DNA often includes structural changes that are indicative of cancer. Such structural changes may be at the level of the chromosome, which includes aneuploidy (abnormal number of chromosomes), duplications, deletions, or inversions, or alterations in sequence. "Tumor fraction" means the fraction of total DNA that is derived from tumor cells.

By "alteration" is meant a change relative to a reference. In one embodiment, a change in sequence (i.e., insertion, deletion, point mutation, copy number alteration (CNA), or loss in heterozygosity (LOH)) is determined relative to a reference sequence, reference exome, and/or reference genome.

In this disclosure, "comprises," "comprising," "containing" and "having" and the like can have the meaning ascribed to them in U.S. Patent law and can mean " includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of this invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By "marker" is meant any protein or polynucleotide having an alteration in sequence, copy number, expression level or activity that is associated with a disease or disorder.

By "neoplasia" is meant a disease that is associated with inappropriately high levels of cell division, inappropriately low levels of apoptosis, or both. For example, cancer is an example of a neoplastic disease. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

A "reference genome" is a defined genome used as a basis for genome comparison or for alignment of sequencing reads thereto. A reference genome may be a subset of or the entirety of a specified genome; for example, a subset of a genome sequence, such as exome sequence, or the complete genome sequence.

By "subject" is meant a mammal, including, but not limited to, a human or non-human mammal, such as a bovine, equine, canine, ovine, rodent, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1E depict copy number and tumor fractions from ULP-WGS. FIG. 1A depicts an exemplary workflow for processing cfDNA for whole-exome sequencing. FIG. 1B depicts genome-wide copy number from 0.1× ULP-WGS of cfDNA from a healthy donor (top panel) and genome-wide copy number from 25× WGS and 0.1× WGS of cell-free DNA from a metastatic breast cancer patient (MBC_315), and 1× WGS and WES of matched tumors from this patient (bottom panels). SCNA for tumor WES and cfDNA 25× coverage WGS were predicted using TITAN (Ha et al. *Genome Res.* 24, 1881-1893 (2014)). FIG. 1C provides a series of graphs showing that reasonably pure cell-free DNA (cfDNA) was obtained from about 700 blood samples screened. Tumor fraction in cfDNA from patients with pancreas adenocarcinoma (PAAD), brain cancer, multiple myeloma (MM), skin cutaneous melanoma (SKCM), small cell lung cancer (SCLC), colon adenocarcinoma (COAD), bladder carcinoma (BLCA), esophageal carcinoma (ESCA), kidney renal clear cell carcinoma (KIRC), stomach adenocarcinoma (STAD), lung adenocarcinoma (LUAD), chronic lymphocytic leukemia (CLL), and ovarian cancer (OV). The error rate of tumor fraction estimation was about 3%, and therefore indicates a lower limit of detection sensitivity at 0.03 tumor fraction from ULP-WGS of cfDNA. The threshold for determining the presence of tumor content in a cfDNA sample from ULP-WGS was set to 0.03 tumor fraction. FIG. 1D depicts plots providing a comparison of copy ratios between ULP-WGS of cfDNA with deep (>10×) WGS of the same cfDNA sample, WGS (1×) of matched tumors from 22 metastatic breast cancer (MBC) patients, and WES (average mean target coverage 173×) of matched tumors from 41 MBC and prostate cancer (CRPC) patients. Log 2 copy ratios were computed as normalized read coverage for each 1 Mb (WGS/ULP-WGS) and the mean of overlapping 50 kb bins (WES) after adjustment for tumor fraction/purity. The correlation of copy ratios between tumor and cfDNA was computed using Spearman rank correlation (coefficient ρ). F-measure (F1) is the harmonic mean of the CNA positive predictive value (precision) and sensitivity (recall) Performance. Recall is defined as the proportion of SCNA gain/loss in tumor biopsy also observed in ULP-WGS of cfDNA. FIG. 1E is a plot showing a comparison of tumor fractions estimated from ULP-WGS and WES of cfDNA. Samples (n=35) with similar tumor ploidy (difference<0.75 and ploidy≥1.5) estimated in both ULP-WGS and tumor WES are shown. The correlation between the two data types was calculated using Pearson correlation (coefficient r). Thin gray line denotes y=x. WES tumor fractions were estimated using ABSOLUTE (shown; Carter et al. *Nat. Biotechnol.* 30, 413-421 (2012)) and TITAN.

FIG. 2A provides copy number profiles for cfDNA WGS (Titan, 1 Mb bins), cfDNA ULP-WGS (1 Mb bin) cfDNA WES (Titan, 50 kb bins), matched tumor biopsy WGS, and matched tumor biopsy WES (Titan, 50 kb bins). Performance was computed based on binary classification metrics of precision and recall for comparisons. FIG. 2B is a plot depicting comparison of normalized copy ratios ($\log_2$) between cfDNA ULP-WGS and deep WGS of the same cfDNA sample. FIG. 2C is a plot depicting comparison of normalized copy ratios ($\log_2$) between cfDNA ULP-WGS and 1× WGS of the tumor biopsy. FIG. 2D is a plot depicting comparison of normalized copy ratios ($\log_2$) between cfDNA ULP-WGS and WES of the tumor biopsy. Biological differences in copy number events in chromosome 10, 13, 19p, and Xq are indicated with arrows. Solid line denotes y=x; dashed line denotes model fit using linear least squares regression.

FIG. 3A depicts plots showing fraction of clonal (≥0.9 cancer cell fraction, CCF) and subclonal (<0.9 CCF) SSNVs detected by MuTect in WES of tumor biopsies and confirmed (i.e. supported by ≥3 variant reads) in WES of cfDNA. Sites with <3 reads that had power <0.9 for mutation calling were not included when computing the fraction of SNVs confirmed. FIG. 3B depicts plots showing fraction of clonal and subclonal SSNVs detected in WES of cfDNA and confirmed in WES of tumor biopsies. For eighteen patients with WES of cfDNA at a second time point $t_2$, SSNVs not detected in the matched tumor biopsy but confirmed at $t_2$ are indicated with black. FIG. 3C depicts plots showing analysis of clonal dynamics in an ER+ breast cancer patient diagnosed with metastatic disease 1.5 years (yrs) prior to biopsy and cfDNA collection ($t_1$, Day 0). Clustering analysis of CCF for SSNVs between matched tumor biopsy and cfDNA ($t_1$) is shown (left panel). The CCF of four mutation clusters are shown, one containing ESR1 L536P (Subclonal Cluster 1, orange) and the other containing ESR1 D538G (Subclonal Cluster 2, light blue), at $t_1$ and $t_2$ (51 days apart) from a patient with ER+ metastatic breast cancer being treated with a SERD (right panel). The lymph node biopsy was taken at the same time as cfDNA $t_1$. Mutations were clustered by the CCFs for each pair of samples using Phylogic (Brastianos et al. *Cell* 164, 57-68 (2016)). Error bars represent the 95% credible interval of the joint posterior density of the clusters. Mutations, excluding indels, having ≥90% estimated power based on coverage in both samples are shown; clusters with fewer than mutations are excluded. The number of mutations in each cluster is indicated in the legend in parentheses.

FIGS. 4A-4E show that genomic alterations of known biological show significance and broad application to large cohorts of metastatic cancer patients. FIG. 4A provides the alteration status of significantly mutated genes predicted by MutSig2CV (Lawrence et al. *Nature* 499, 214-218 (2013); Lawrence et al. *Nature* 505, 495-501 (2014)) and known cancer-associated genes (Van Allen et al. *Nat. Med.* 20, 682-688 (2014)) are shown for cfDNA and tumor biopsies from 27 metastatic breast cancer (MBC) patients. Mutated genes with MutSig2CV q-value<0.1 are statistically significant. Mutations that were exclusively detected in one sample may be present at low CCF in the other matched sample but were excluded from the frequency calculation. Mutations were predicted using MuTect. FIG. 4B provides the alteration status of significantly mutated genes predicted by focal SCNAs and known cancer-associated genes (Van Allen et al. *Nat. Med.* 20, 682-688 (2014)) are shown for cfDNA and tumor biopsies from 27 metastatic breast cancer (MBC) patients. SCNA frequencies were computed for oncogenes (MYC to ERBB2) and tumor suppressors (BRCA1 to ATM) using only amplification and deletion status, respectively. SCNAs were predicted using ReCapSeg and ABSOLUTE. FIG. 4C are plots depicting mutational signatures in whole-exome sequencing of cfDNA and tumor biopsies predicted using a Bayesian non-negative matrix factorization (NMF) approach (Kim et al. *Nat. Genet.* 48, 600-606 (2016)). Samples with predicted homozygous loss of BRCA1/2 are indicated in light gray and dark gray. Black line denotes y=x; blue line denotes model fit using linear least squares regression. FIG. 4D is a plot depicting neoantigen burden, defined as the number of predicted neoantigen SSNVs, calculated using NetMHCpan (Hoof et al. *Immunogenetics* 61, 1-13 (2009)). Black line denotes y=x; thin gray line denotes model fit using linear least squares regression. FIG. 4E is a graph showing broad applicability of the invention to many patients with metastatic cancer. Tumor fractions estimated from ULP-WGS of cfDNA from 913 blood samples from 391 patients with metastatic breast cancer and 579 blood samples from 129 patients with metastatic prostate cancers. The maximum tumor fraction across all samples for each patient is shown. Samples with coverage<0.05× were excluded.

FIGS. 5A-5D show an analysis of ULP-WGS tumor fraction and large-scale SCNAs. FIG. 5A depicts ULP-WGS tumor fraction estimates for 1492 metastatic breast (MBC) and prostate (CRPC) cancer samples. Samples with ≥0.10 (blue), ≥0.03 and <0.10 (black), and <0.03 (grey) tumor fraction are indicated. FIG. 5B depicts plots showing fraction of patients having ≥0.1 tumor fraction, divided into groups containing 1, 2, or ≥3 number of plasma samples collected. The total number of samples (n) within each of the three groups are indicated. FIG. 5C depicts gene-based frequencies of copy number alterations among patients with metastatic breast cancer predicted from ULP-WGS of cfDNA. FIG. 5D depicts gene-based frequencies of copy number alterations among patients with prostate cancer predicted from ULP-WGS of cfDNA. Gene alterations were defined based on overlapping SCNA segments predicted from normalized read coverage at 1 Mb bins. Only samples with ≥0.10 are included.

FIGS. 6A-6E show the use of ULP-WGS of cfDNA to characterize and monitor a patient's response to therapy. FIG. 6A shows copy number alteration (CNA) profiles over time characterized using ultra-low pass whole genome sequencing of cell free DNA (ULP-WGS of cfDNA) of a metastatic prostate cancer patient. Interestingly, ULP-WGS of cfDNA provides an early readout of response to therapy. Few detectable copy number alteration events were observed and estimate tumor fraction (purity) was 4% at week 0, the initial time of treatment (top panel). Increased cfDNA yield and estimated tumor fraction was observed at week 4 during a second cycle of treatment (second panel from top), which may provide early indications of increased tumor burden. In week 40 and 44, the cfDNA yields, number of copy number alteration events, and tumor fractions increased, consistent with clinical progression status and prostate serum antigen (PSA), which is an established biomarker of prostate cancer (bottom two panels). FIG. 6B shows copy number alteration (CNA) profiles characterized over time using ultra-low pass whole genome sequencing of cell free DNA (ULP-WGS of cfDNA) of a metastatic prostate cancer patient. The top panel shows a CNA profile at week 0 with an increased number of detectable CNAs and high estimated tumor fraction relative to week 20. This result is consistent with the patient's clinical response to treatment at week 20. FIG. 6C shows copy number alteration (CNA) profiles characterized over time using ultra-low pass whole genome sequencing of cell free DNA (ULP-WGS of cfDNA) of a metastatic prostate cancer patient. In weeks 0, 4, and 33 (top three panels), the estimated tumor fraction from ULP-WGS was consistent with the patient's lack of clinical response to targeted treatment, despite having stable PSA. Upon a switch to chemotherapy at week 36, the patient responded and this was reflected in the tumor fraction estimate from ULP-WGS. Subsequent analysis of cfDNA from blood in week 43 confirmed the decreased tumor fraction which was consistent with the patient's continued response to chemotherapy. Interestingly, the PSA remained relatively stable throughout the entire 43 weeks. These results highlight an example in which ULP-WGS of cfDNA provides a more consistent readout of response to therapy than the established biomarker, PSA. FIG. 6D shows copy number alteration (CNA) profiles characterized over time using ultra-low pass whole genome sequencing of cell free DNA (ULP-WGS of cfDNA) of a metastatic prostate cancer patient. Despite initial treatment at week 0, no reduction in CNA is observed at week 10. Estimated tumor fractions (purity) from ULP-WGS increased in week 17, which was consistent with clinical progression. This supports the use of ULP-WGS of cfDNA as an early readout of response to therapy. FIG. 6E shows copy number alteration (CNA) profiles characterized over time using ultra-low pass whole genome sequencing of cell free DNA (ULP-WGS of cfDNA) of a metastatic prostate cancer patient. The estimated tumor fraction from ULP-WGS decreased at week 8, which is consistent with the patient's clinical response to therapy. Continued monitoring at week 16 shows an increase in estimated tumor fraction, PSA, and cfDNA yield. These results may provide an early indication of eventual progression of cancer. Indeed, in week 20, the patient's cancer was clinically progressing. These results support the use of ULP-WGS of cfDNA as an early readout of response to therapy.

DETAILED DESCRIPTION OF THIS INVENTION

Figure 1A:
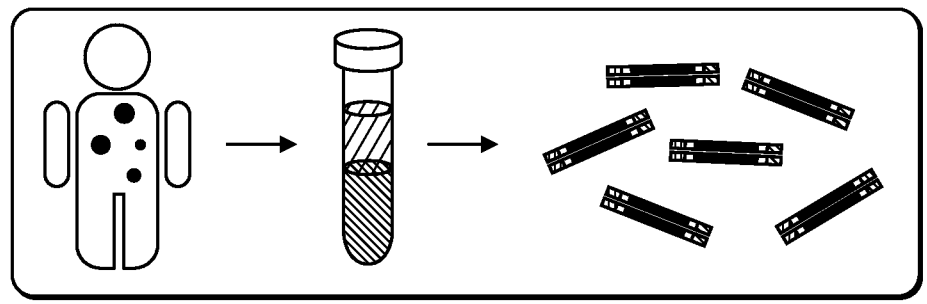
Figure 1A:
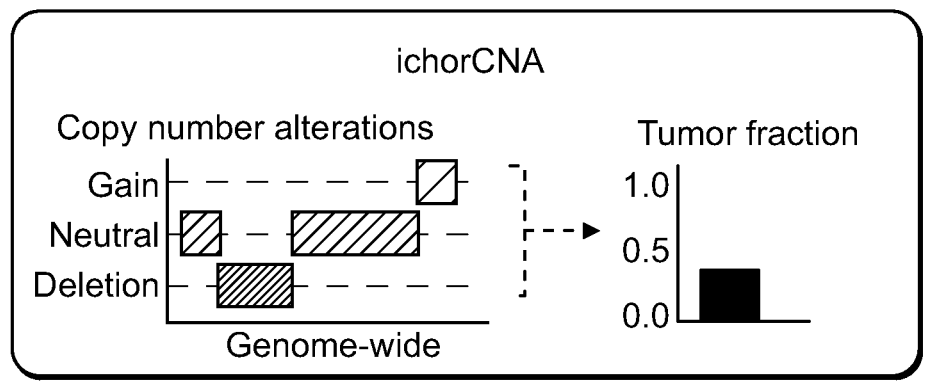
Figure 1A:
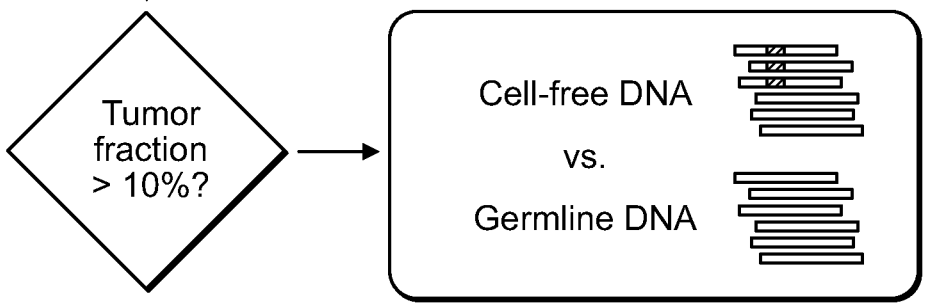
Figure 1A:

The invention generally provides methods of using low coverage sequencing to assess the relative fraction of tumor versus normal DNA in a sample, and to assess copy number alterations present in the sample.

The invention provides an efficient process to qualify DNA samples for whole-exome and/or whole genome sequencing based on tumor fraction (or tumor content). Without being bound by theory, the power to detect a variant at a particular sequencing depth depends on the tumor fraction of a sample. The selected samples can then be used to systematically compare the somatic mutations, indels, and copy number alterations detected in whole exome or whole genome sequencing of cfDNA to whole exome or whole genome sequencing of matched tumor biopsies. Advantageously, methods of the invention provide for ultra-low-pass sequencing (i.e., about 0.01, 0.05, 0.1, 0.5, 1, 2, 3, or 5× genome or exome wide sequencing coverage) for assessing tumor fraction and samples for which sufficient tumor content is estimated, whole exome sequencing of cfDNA can be performed. Among patients with metastatic breast or prostate cancers, whole exome sequencing of cfDNA was found to uncover 91% of the clonal mutations, 59% of the subclonal mutations, and 86% of the clonal copy number alterations (CNA) and 80% of the subclonal CNAs detected in whole exome sequencing of matched tumor biopsies. The high concordance suggests that comprehensive sequencing of cfDNA may enable genomic discovery in a routine and minimally invasive manner.

This invention overcomes the challenge of screening large numbers of blood samples to assess how much tumor-derived cell-free DNA is present in blood plasma. This allows estimation of the fraction of tumor DNA in a sample from a trivial amount of sequencing (~0.1× coverage or roughly $20 of sequencing coverage). This also provides for the detection of copy number alterations at a 500 kb scale that can be detected in the sample. This serves not only as an efficient way to qualify samples for targeted or whole-exome/whole-genome sequencing for cancer genomics discoveries, but also correlates with therapeutic response and enables the study of copy number alterations in large cohorts.

The invention provides for characterization of the malignant status of a sample or for diagnosis of cancer in the subject from whom the sample is derived. Based on the detection of somatic, tumor-specific copy number alterations from DNA of a sample, the fraction of tumor DNA is estimated. cfDNA and germline DNA was isolated from blood and analyzed using low coverage sequencing to estimate tumor content based on genome-wide copy number. The CNA events and tumor fraction were simultaneously predicted in a unified Bayesian hidden Markov model (HMM) framework. The estimated error rate of tumor fraction estimation was about 0.03 at genome sequencing coverage of 0.1×, as determined from application to healthy donor samples, which should have an expected 0.00 tumor fraction. Therefore, samples having greater than 0.03 tumor fraction, due to the harboring detectable CNA events, are classified as tumor-derived.

In related applications, the methods described herein can be used to assess the tumor cellularity (purity) of tumor biopsies of human primary cancers with high stromal contamination and lymphocytic infiltration. Where little tumor DNA is present, methods of the invention can be used to assess whether sequencing is warranted. This would avoid the sequencing of samples that have little tumor content, which would provide significant cost saving. In addition, the methods of the invention could be used to assess the fraction of tumor relative to normal cells present in a tissue sample to be used for cell line generation. This would avoid the propagation of cell lines from human primary tumors that are largely composed of normal cells rather than of tumor cells.

Whole Genome Sequencing and Whole Exome Sequencing

Whole genome sequencing (also known as "WGS", full genome sequencing, complete genome sequencing, or entire genome sequencing) is a process that determines the complete DNA sequence of an organism's genome. A common strategy used for WGS is shotgun sequencing, in which DNA is broken up randomly into numerous small segments, which are sequenced. Sequence data obtained from one sequencing reaction is termed a "read." The reads can be assembled together based on sequence overlap. The genome sequence is obtained by assembling the reads into a reconstructed sequence.

Whole exome sequencing ("WES") is a technique used to sequence all the expressed genes in a genome (known as the exome). It includes first selecting only the subset of DNA that encodes proteins (exons), and then sequencing the exons using any DNA sequencing technology well known in the art or as described herein. In a human being, there are about 180,000 exons, which constitute about 1% of the human genome, or approximately 30 million base pairs. To sequence the exons of a genome, fragments of double-stranded genomic DNA are obtained (e.g., by methods such as sonication, nuclease digestion, or any other appropriate methods). Linkers or adapters are then attached to the DNA fragments, which are then hybridized to a library of polynucleotides designed to capture only the exons. The hybridized DNA fragments are then selectively isolated and subjected to sequencing using any sequencing method known in the art or described herein.

In one embodiment, the sequencing of a DNA fragment is carried out using commercially available sequencing technology SBS (sequencing by synthesis) by Illumina. In another embodiment, the sequencing of the DNA fragment is carried out using chain termination method of DNA sequencing. In yet another embodiment, the sequencing of the DNA fragment is carried out using one of the commercially available next-generation sequencing technologies, including SMRT (single-molecule real-time) sequencing from Pacific Biosciences, Ion Torrent™ sequencing from ThermoFisher Scientific, Pyrosequencing (454) from Roche, and SOLiD® technology from Applied Biosystems. Any appropriate sequencing technology may be chosen for sequencing.

This invention provides methods for qualifying a DNA sample for whole exome sequencing after ultra low pass (ULP)-whole genome sequencing. In one embodiment, the fraction of cells affected by a disease, such as cancer, may be estimated using one or more of the statistical models described herein. The qualifying process involves selecting a DNA sample having a tumor fraction greater than a threshold value, e.g. 5%, for whole exome sequencing (WES). Understanding the fraction of tumor-derived DNA in a sample allows one to adjust the depth of sequencing used in WES or other deeper sequencing. For instance, if a sample has a very low purity of tumor-derived DNA, a much greater depth of sequencing may be required to achieve the same sensitivity for detection of somatic alterations (Cibulskis et al. *Nat. Biotechnol.* 31, 213-219 (2013)).

Ultra low pass sequencing advantageously provides for the accurate characterization of genomic or exomic DNA at a significant savings of cost and time, thereby obviating the need for complete integrative clinical sequencing of the whole-exome, matched germline, and/or transcriptome as practiced, for example, by Robinson et al., *Cell* 161:1215-1228, 2015 where meant target coverage for tumor exomes was 160× and for matched normal exomes was 100×.

As used herein, the term "coverage" refers to the percentage of genome covered by reads. In one embodiment, low coverage or ultra low pass coverage is less than about 1×. Coverage also refers to, in shotgun sequencing, the average number of reads representing a given nucleotide in the reconstructed sequence. It can be calculated from the length of the original genome (G), the number of reads(N), and the average read length(L) as N×L/G. Biases in sample preparation, sequencing, and genomic alignment and assembly can result in regions of the genome that lack coverage (that is, gaps) and in regions with much higher coverage than theoretically expected. It is important to assess the uniformity of coverage, and thus data quality, by calculating the variance in sequencing depth across the genome. The term depth may also be used to describe how much of the complexity in a sequencing library has been sampled. All sequencing libraries contain finite pools of distinct DNA fragments. In a sequencing experiment only some of these fragments are sampled.

Alterations of Cancer Genome

Alterations of the genome have been identified in virtually all cancers. These alterations may include, without limitation, gene mutation, loss of heterozygosity (LOH), changes in chromosome number (aneuploidy), deletions, insertions, inversions, translocations, amplifications, and copy number alterations (CNA). Detection of copy number alterations is useful for characterizing the malignant status of a tumor, diagnosis of cancer, assessment of the purity in tumor biopsies of human primary cancers, and qualifying samples for additional characterization, such as whole exome sequencing.

This invention provides methods to characterize alterations present in a cancer genome. In one embodiment, this invention involves isolating cfDNA from a biological sample, sequencing the DNA using ULP-WGS, analyzing the sequence of the DNA using statistical models described herein, and characterizing the copy number alterations present in the cfDNA, for example, by generating a copy number alteration profile. In one embodiment, the CNA profile is used to determine the tumor fraction of a sample. In another embodiment, the invention provides a method of diagnosing cancer in a subject by detecting the CNA profile of sample from the subject. In yet another embodiment, the invention provides a method of identifying a treatment and/or an agent for treatment and/or prevention of a cancer by characterizing CNAs present in cfDNA of the subject. In one embodiment, the method involves comparing the CNAs profiles before and after the treatment and/or administration of the agent.

The methods of the invention are applicable to any disease and/or disorder having copy number alterations.

Statistical Methods

To analyze ULP-WGS data, a modified approach from the TITAN (Ha G. et al., *Genome Res.* 24, 1881-1893 (2014) ("Ha 2014")), the content of which is incorporated by reference in its entirety. The approach in this invention employs a hidden Markov model that simultaneously performs segmentation, copy number prediction, and purity (also termed tumor fraction) and ploidy estimation. This approach is optimized for increased sensitivity to detect events from low purity tumor-derived DNA in the absence of a control sample by using fine-tuned Bayesian priors and considering all CNA events in a unified probabilistic model. TITAN code is available at http://compbio.bccrc.ca/software/titan/ and https://github.com/gavinha/TitanCNA and HMMcopy frameworks and pipelines needed to be adapted. This new approach overcomes major challenges that TITAN/HMMcopy, and all other existing tools, were not designed to address: 1) ultra low coverage (0.1×) sequencing (most tools are optimized for WGS of 20× or greater); 2) unavailable matched germline normal sample as control (many tools require heterozygous SNPs determined from normal); 3) very low tumor content in DNA samples such as in cell-free DNA (many tools advertise benchmarks for reasonable performance at 0.15-0.20 tumor fractions). The landscape of the alterations of the cancer genome may be inferred from such estimates.

Types of Samples

This invention provides methods to extract and sequence a polynucleotide present in a sample. In one embodiment, the samples are biological samples generally derived from a human subject, preferably as a bodily fluid (such as blood, plasma, serum, cerebrospinal fluid, phlegm, saliva, urine, semen, prostate fluid, breast milk, or tears, or tissue sample (e.g. a tissue sample obtained by biopsy). In a further embodiment, the samples are biological samples derived from an animal, preferably as a bodily fluid (such as blood, cerebrospinal fluid, phlegm, saliva, or urine) or tissue sample (e.g. a tissue sample obtained by biopsy). In still another embodiment, the samples are biological samples from in vitro sources (such as cell culture medium). CfDNA attached to a substrate may be first suspended in a liquid medium, such as a buffer or a water, and then subject to sequencing and/or analysis. In yet another embodiment, the sample contains DNA within a cell, which may be extracted, sequenced and subject to the same analysis for landscape of alterations of genome.

Patient Monitoring

The disease state or treatment of a patient having a cancer or disease characterized by copy number alterations can be monitored using the methods and compositions of this invention. In one embodiment, the response of a patient to a treatment can be monitored using the methods and compositions of this invention. Such monitoring may be useful, for example, in assessing the efficacy of a particular treatment in a patient. Treatments amenable to monitoring using the methods of the invention include, but are not limited to, chemotherapy, radiotherapy, immunotherapy, and surgery. Therapeutics that alter the CNA landscape of cfDNA are taken as particularly useful in this invention. In one embodiment, methods of the invention are used to monitor PTEN loss or treatment with PARP inhibitors (e.g., iniparib, talazoparib, olaparib, rucparib, veliparib, MK 4827, BGB-290).

Diagnostics

Neoplastic tissues display alterations in their genome compared to corresponding normal reference tissues. Copy number alterations are correlated with neoplasia. Accordingly, this invention provides methods for detecting, diagnosing, or characterizing a neoplasia in a subject. The present invention provides a number of diagnostic assays that are useful for the identification or characterization of a neoplasia.

In one approach, diagnostic methods of the invention are used to detect the CNA in a biological sample relative to a reference (e.g., a reference determined by an algorithm, determined based on known values, determined using a standard curve, determined using statistical modeling, or level present in a control polynucleotide, genome or exome).

Methods of the invention are useful as clinical or companion diagnostics for therapies or can be used to guide treatment decisions based on clinical response/resistance. In other embodiments, methods of the invention can be used to qualify a sample for whole-exome sequencing.

A physician may diagnose a subject and the physician thus has the option to recommend and/or refer the subject to seek the confirmation/treatment of the disease. The availability of high throughput sequencing technology allows the diagnosis of large number of subjects.

The practice of the present invention employs, unless otherwise indicated, conventional techniques of molecular biology (including recombinant techniques), microbiology, cell biology, biochemistry and immunology, which are well within the purview of the person of ordinary skill. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of this invention, and, as such, may be considered in making and practicing this invention. Particularly useful techniques for particular embodiments will be discussed in the sections that follow.

The following examples are put forth so as to provide those of ordinary skill in the art with a complete disclosure and description of how to make and use the assay, screening, and therapeutic methods of this invention, and are not intended to limit the scope of what the inventors regard as their invention.

EXAMPLES

Example 1

Ultra-Low-Pass Whole-Genome Sequencing can be Used to Characterize Tumor Content in a cfDNA Library A low-cost, sample-conserving, and unbiased approach to screen cell-free DNA libraries prior to whole exome sequencing would help to focus whole exome sequencing on libraries with detectable tumor DNA. While many previous approaches to screening for cancer-derived cfDNA have focused on targeted mutation detection, it was hypothesized that using somatic copy number alterations would be more generally applicable as the vast majority of metastatic cancers harbor arm-level somatic SCNAs (citation) whereas different tumor types may have few recurrent somatic mutations. Additionally, copy number detection is an unbiased approach which borrows statistical strength from genome-wide signals while somatic mutation detection relies on high coverage at targeted regions to achieve high sensitivity in low purity samples. The question of whether ultra-low-pass whole-genome sequencing (ULP-WGS) could sensitively detect large-scale SCNAs and be used to estimate tumor fractions was explored. This would only require a small fraction of each library (~1%) and conserve enough DNA for hybrid selection.

An analytical approach termed "ichorCNA" was developed to quantify tumor fraction in cfDNA without prior knowledge of single nucleotide variants (SSNVs) or somatic copy number alterations (SCNAs) in patients' tumors from ULP-WGS (FIG. 1A, https://github.com/broadinstitute/ichorCNA). ichorCNA was applied to determine which cfDNA samples had sufficient tumor content (>10%) for whole-exome sequencing. Subsequent analysis of whole-exome sequencing of cell-free DNA and matched tumor biopsies from 41 patients demonstrated that cell-free DNA provided a suitable proxy for a tumor biopsy. Further examination of 1,492 blood samples from 520 patients with metastatic breast or prostate cancer using ichorCNA revealed 44% of patients had sufficient tumor fraction for standard depths of whole-exome sequencing of cell-free DNA.

An exemplary process begins with patient blood collection, separation of plasma from blood, extraction of cfDNA from plasma and germline DNA from blood, and construction of cfDNA libraries (FIG. 1A). As illustrated in FIG. 1A, ULP-WGS involves separation of plasma from blood, extraction of cfDNA and gDNA, quantification, library construction, ultra-low-pass whole-genome sequencing (ULP-WGS) of cfDNA libraries, and whole exome sequencing of both cfDNA and gDNA libraries. QiaSymphony was used for automated extraction. The size distribution of cell-free DNA was consistent with previous reports. Automated quantification of total cell-free DNA was performed using PicoGreen.

It was found that the size distribution and yields of cfDNA from metastatic cancer patients (median=7.39, range=0.20 to 547.82 ng/mL plasma, n=1642) and healthy donors (median=2.64, range=0.55 to 21.27 ng/mL plasma, n=27) were consistent with previous reports (Snyder et al. *Cell* 164, 57-68 (2016); Szpechcinski et al. *Br. J. Cancer* 113, 476-483 (2015)). Whole-genome libraries were constructed from samples using just 4 mL of plasma—the amount of plasma in a single tube of blood. A library construction protocol was optimized for 5 ng of cfDNA input; 96.3% of cancer patients and 81.4% of healthy donors had ≥5 ng of cfDNA per 4 mL of plasma. Only 1% of each cfDNA sequencing library was then used for ULP-WGS to screen for tumor content. This process resulted in cfDNA and germline DNA libraries suitable for hybrid selection and whole-exome sequencing.

ichorCNA simultaneously predicted segments of SCNA and estimates of tumor fraction while accounting for subclonality and tumor ploidy. To evaluate the performance of ichorCNA, ULP-WGS of cfDNA (FIGS. 1B, 1C) and whole-genome sequencing of cfDNA (10x-48x, n=7) and matched tumor biopsies (1x, n=22) from metastatic breast and prostate cancer patients and healthy donors was used as benchmark datasets (FIGS. 1C, 2A-2D). Highly concordant megabase-scale copy number (sensitivity>0.92, FIG. 1D) was found, including identification of chromothripsis. Tumor fraction estimates from ULP-WGS of cfDNA were also concordant with WGS of the same sample.

To further evaluate how ULP-WGS of cfDNA compares with the metastatic tumor, standard whole-exome sequencing was performed on matched tumor biopsies (average mean target coverage 173x) from 41 patients with metastatic breast and prostate cancers who had a cfDNA sample with ≥0.1 tumor fraction. The majority of large-scale (>1 Mb) SCNAs detected by ULP-WGS of cfDNA were present in the metastatic tumors (median sensitivity 0.82, Spearman ρ=0.66, FIG. 1D).

A series of benchmarking datasets were generated using in silico mixing of up to 50 cancer patient and 22 healthy donor cfDNA samples to generate. The benchmarking datasets demonstrated accurate estimation of tumor fraction (median absolute deviation of error <0.014) and detection of SCNAs at 0.1x coverage. Furthermore, a lower limit of detection of 0.03 tumor fraction was determined, using only a single arm-level (>100 Mb) gain and loss of one copy to detect the presence of tumor. These results indicate that the application of ichorCNA to ULP-WGS of cfDNA offers an accurate approach to detect SCNAs that are reflective of tumor biopsies and provides accurate estimates of tumor fractions, potentially even in cancer types with few SCNAs.

Whole-exome sequencing of cfDNA (average mean target coverage 191x) from the same 41 patients with matched metastatic breast and prostate tumor biopsies was performed and somatic alterations (SSNVs and SCNAs) were detected. First, ULP-WGS and whole-exome sequencing of cfDNA were compared and high concordance of tumor fraction estimates (Pearson's r=0.94, FIG. 1E) and predicted SCNAs (median F-measure=0.95) was found. Furthermore, the predicted number of alterations in cfDNA and metastatic biopsies for non-silent SSNVs (median 50 vs 63) and the genome altered by SCNA (47% vs 44%) were consistent (Wilcoxon rank-sum test p>0.5), which are similar to previous reports for these tumor types (Robinson et al. *Cell* 161, 1215-1228 (2015); Grasso et al. *Nature* 487, 239-243 (2012)). Whole-exome sequencing of cfDNA from 12 healthy donors (average mean target coverage 126x) was also performed and a low false positive rate of SSNVs (median 0.03 non-silent SNVs/Mb) and SCNAs (median $4.25 \times 10^{-5}$ fraction of genome altered) was observed, confirming high specificity of the algorithms. These data indicate that whole-exome sequencing of cfDNA provide similar SCNA results as ULP-WGS of cfDNA, exhibits very low false positive rates for SSNVs and SCNAs, and uncovers similar mutation rates compared to tumor biopsies.

Example 2

Figure 1B:
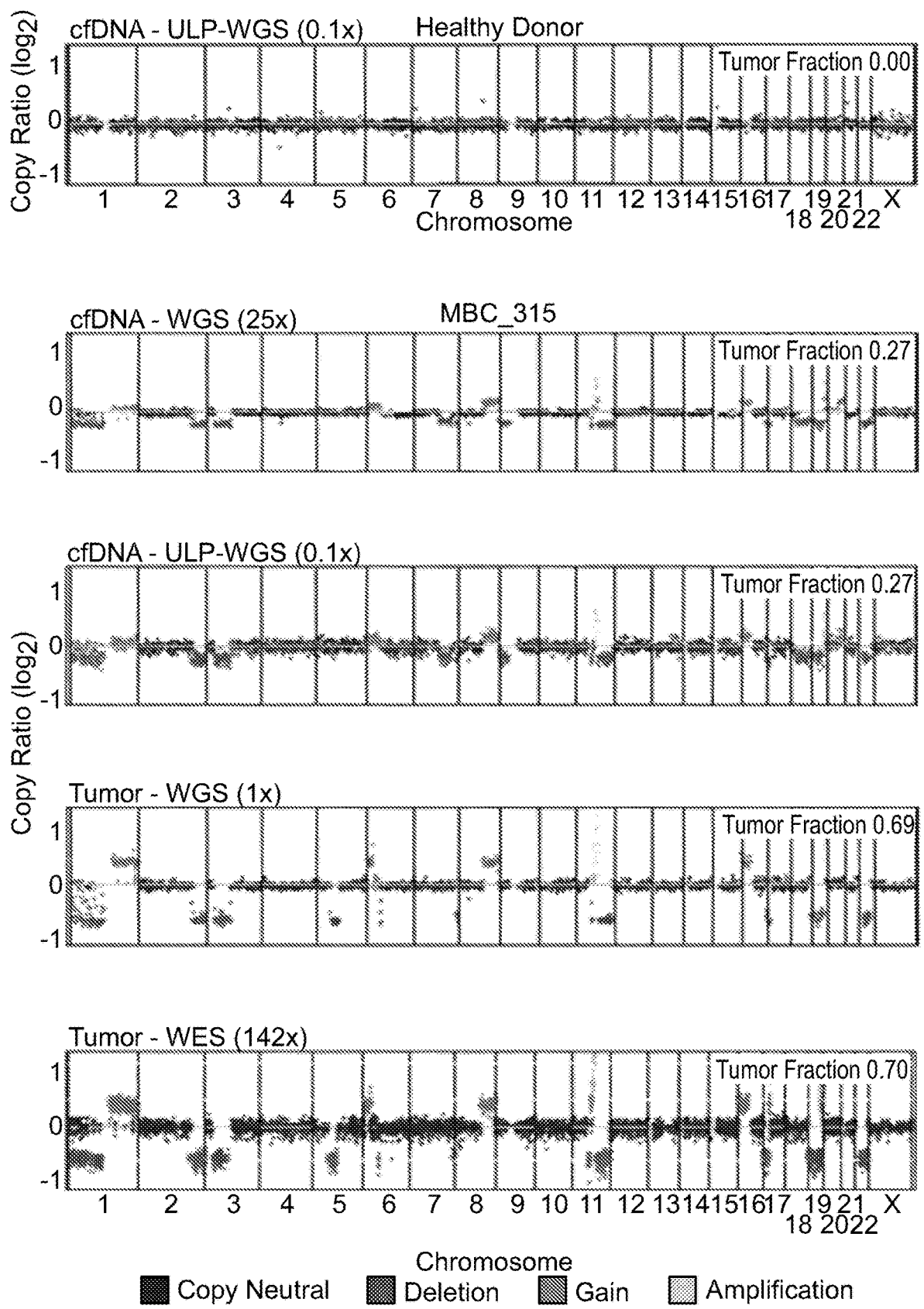
Figure 1D:
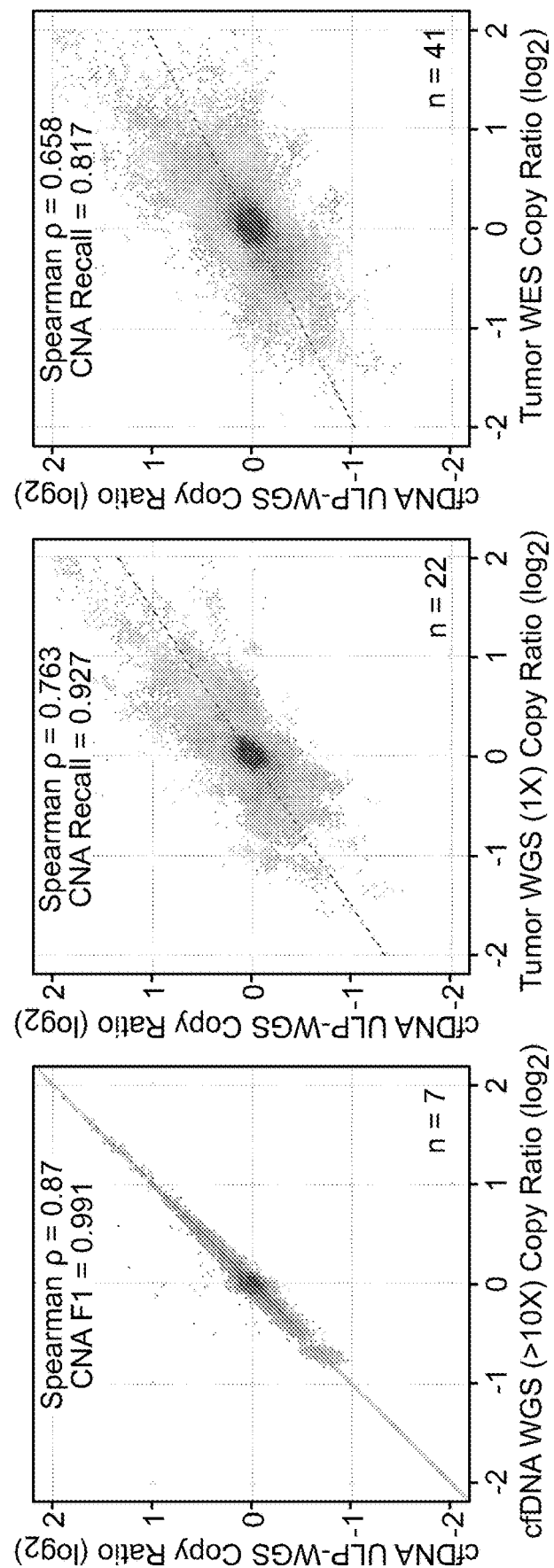

ULP-WGS Offers an Efficient Way to Screen cfDNA Libraries for Tumor Content Prior to Whole Exome Sequencing To validate the ULP-WGS approach for screening of cfDNA libraries from cancer patients, blood and matched tumor biopsies were collected from patients with metastatic breast cancer and patients with metastatic prostate cancer. ULP-WGS of cell-free DNA was performed. Cell-free DNA from cancer patient samples harbored SCNAs above 5 Mb, whereas cell-free DNA from healthy donors lacked large-scale copy number alterations events (FIG. 1B). ULP-WGS data was analyzed and an estimate of tumor fraction was obtained. The majority of patients with metastatic breast and prostate cancer had detectable tumor fractions of cfDNA (>0.03). Importantly, samples from patients with metastatic breast and prostate cancers, respectively, had a tumor fraction of greater than 0.10 in cell-free DNA. 43 cfDNA libraries were selected with a tumor fraction of at least 0.06 and performed whole exome sequencing of cfDNA. Tumor fraction estimates from ULP-WGS were validated by comparison to tumor fractions calculated using established methods, ABSOLUTE (Carter et al. 2012) and TITAN (Ha et al. 2014), on whole exome sequencing of the same libraries. FIG. 1C indicates the tumor fractions detected in cfDNA from hundreds of patients with different types of metastatic cancer using the ULP-WGS approach described herein.

Figure 1E:
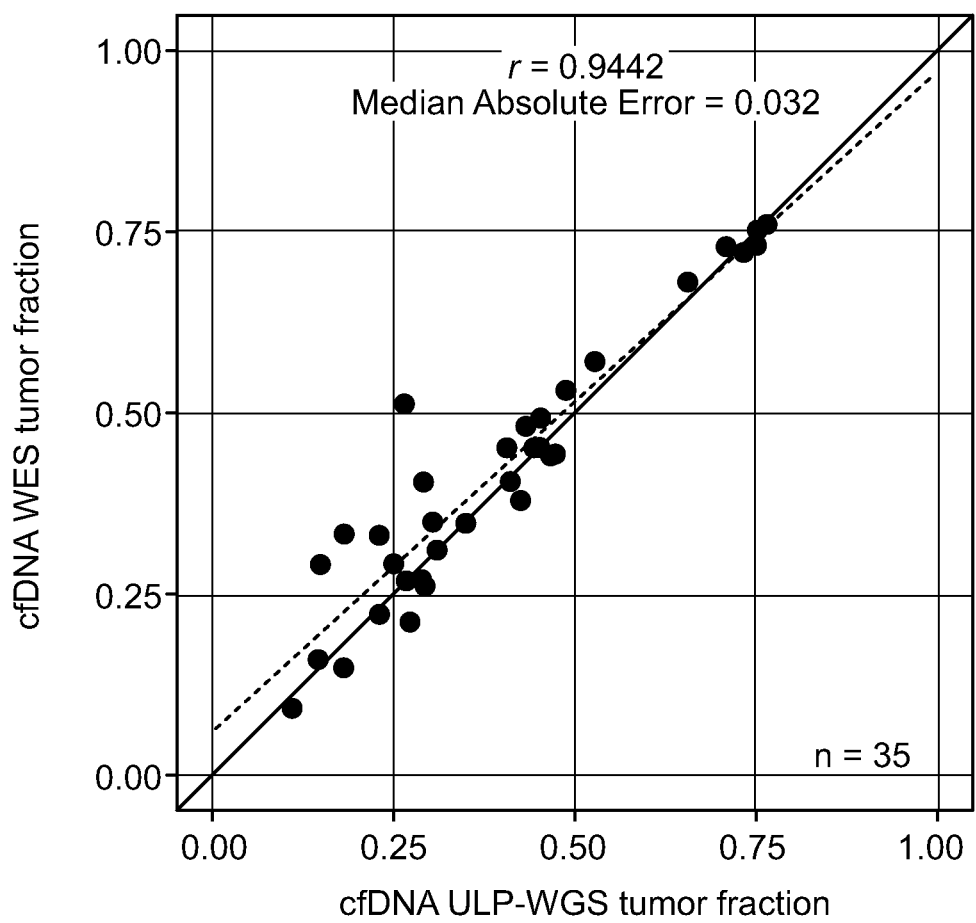
Figures 2, 2A:
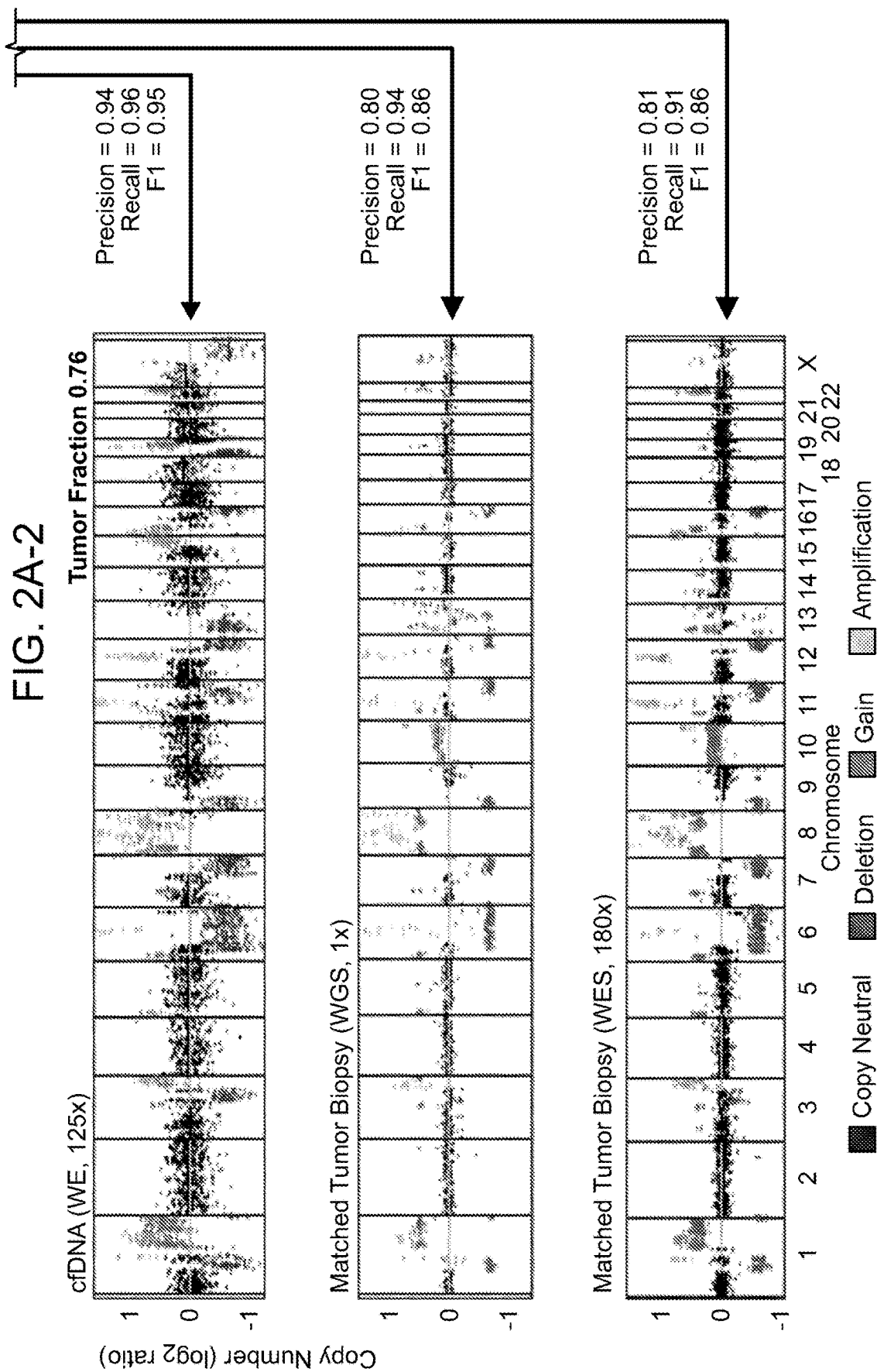
FIGS. 2A-2D show performance of ULP-WGS (0.1×) compared to the deeper sequencing of the same cfDNA sample (10× WGS and WES) and the matched tumor biopsy (1× WGS and WES) for patient MBC_288.
Figure 2B:
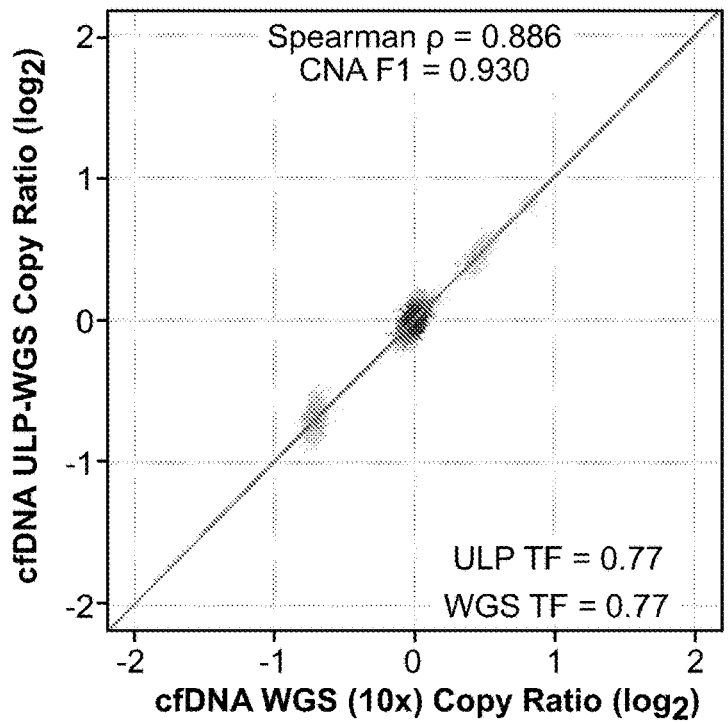
Figure 2C:
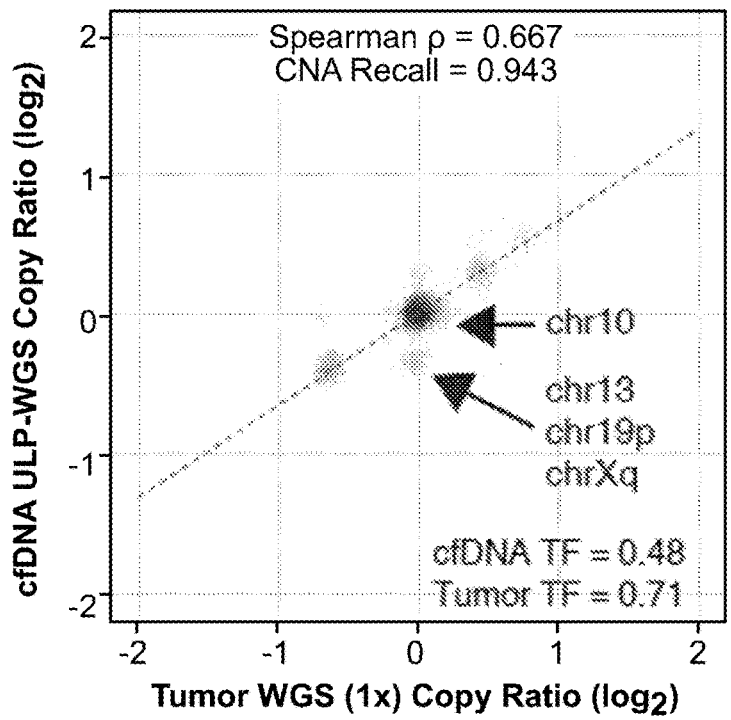
Figure 2D:
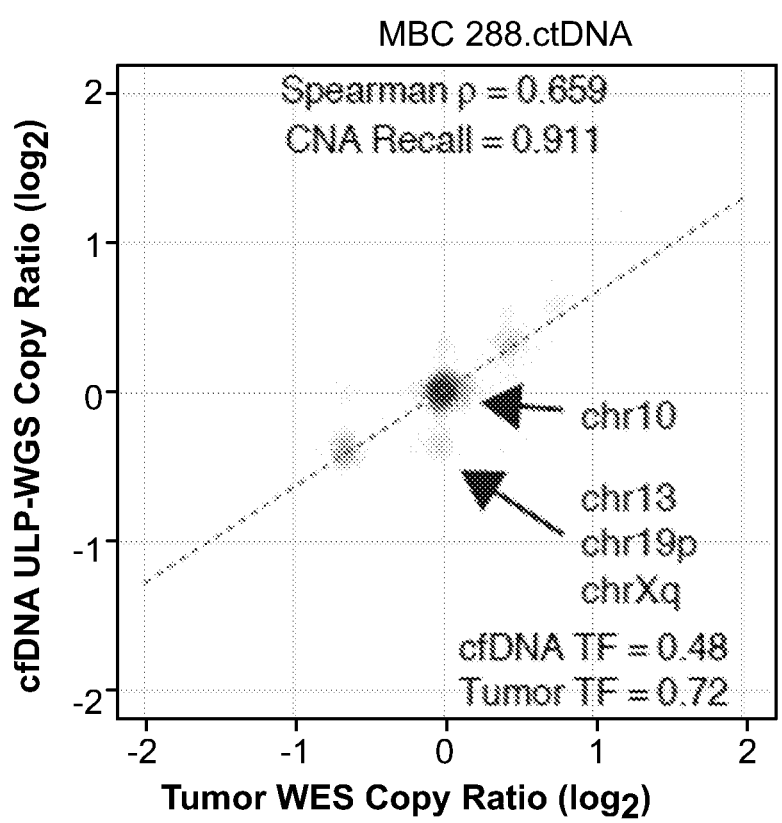

The ULP-WGS and whole exome sequencing tumor fraction estimates were correlated with statistical significance (Pearson's r=0.86, p<0.01, FIG. 1C). The detection of copy number alterations from ULP-WGS also demonstrated high prediction performance from simulations and comparisons to whole exome sequencing across a range of tumor fractions and sequencing coverage. FIG. 1E demonstrates the concordance of tumor fraction estimates from ultra-low-pass whole-genome sequencing (ULP-WGS) obtained using methods of the invention with deeper coverage sequencing and calculation using established methods such as ABSOLUTE. These results indicate that ULP-WGS offers an efficient way to screen cfDNA libraries for tumor content prior to whole exome sequencing.

Example 3

Figures 2, 3A:
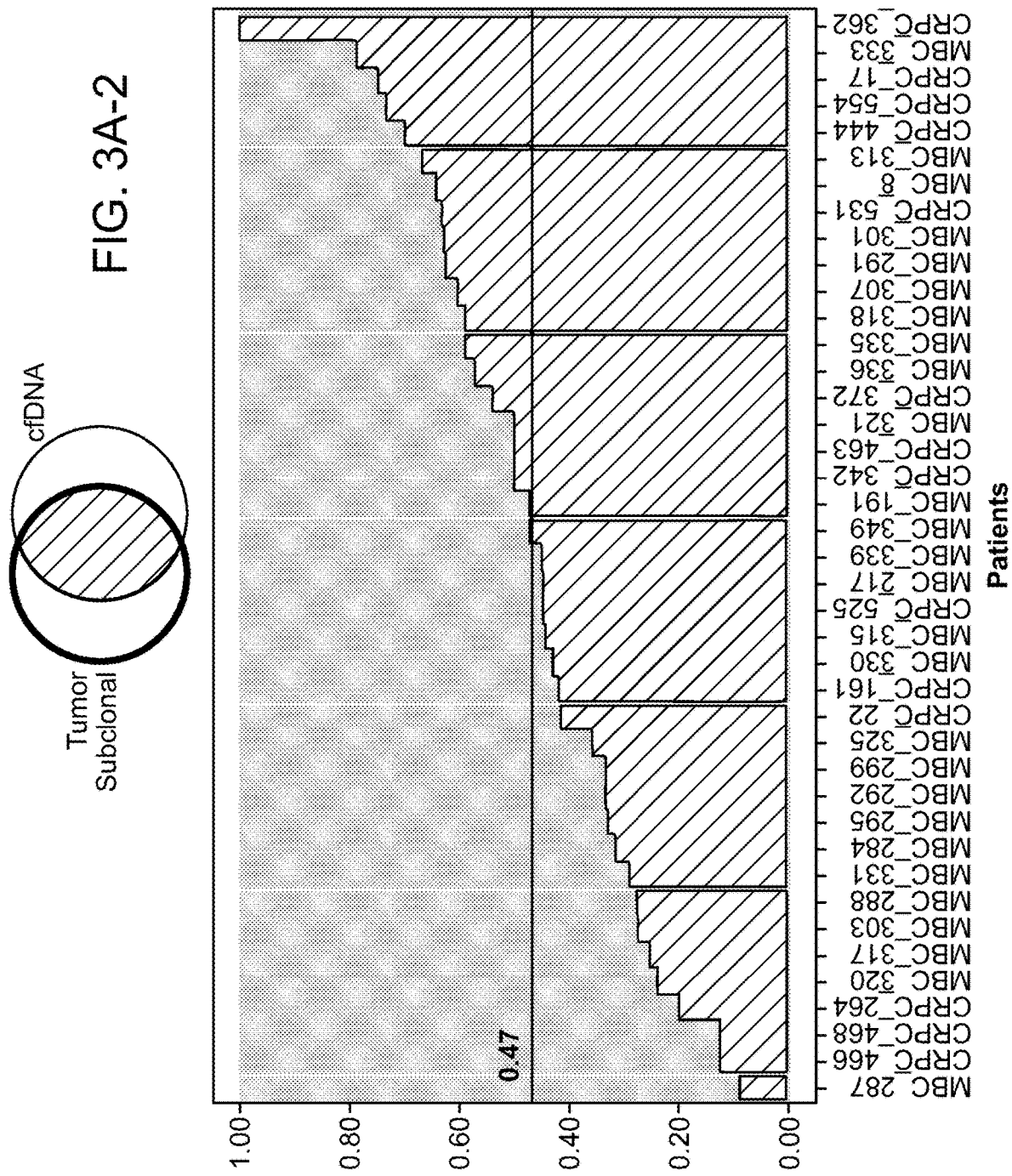
FIGS. 3A-3C depict a comparison of whole-exome sequencing of cfDNA to whole-exome sequencing of matched tumor biopsies.
Figures 2, 3B:
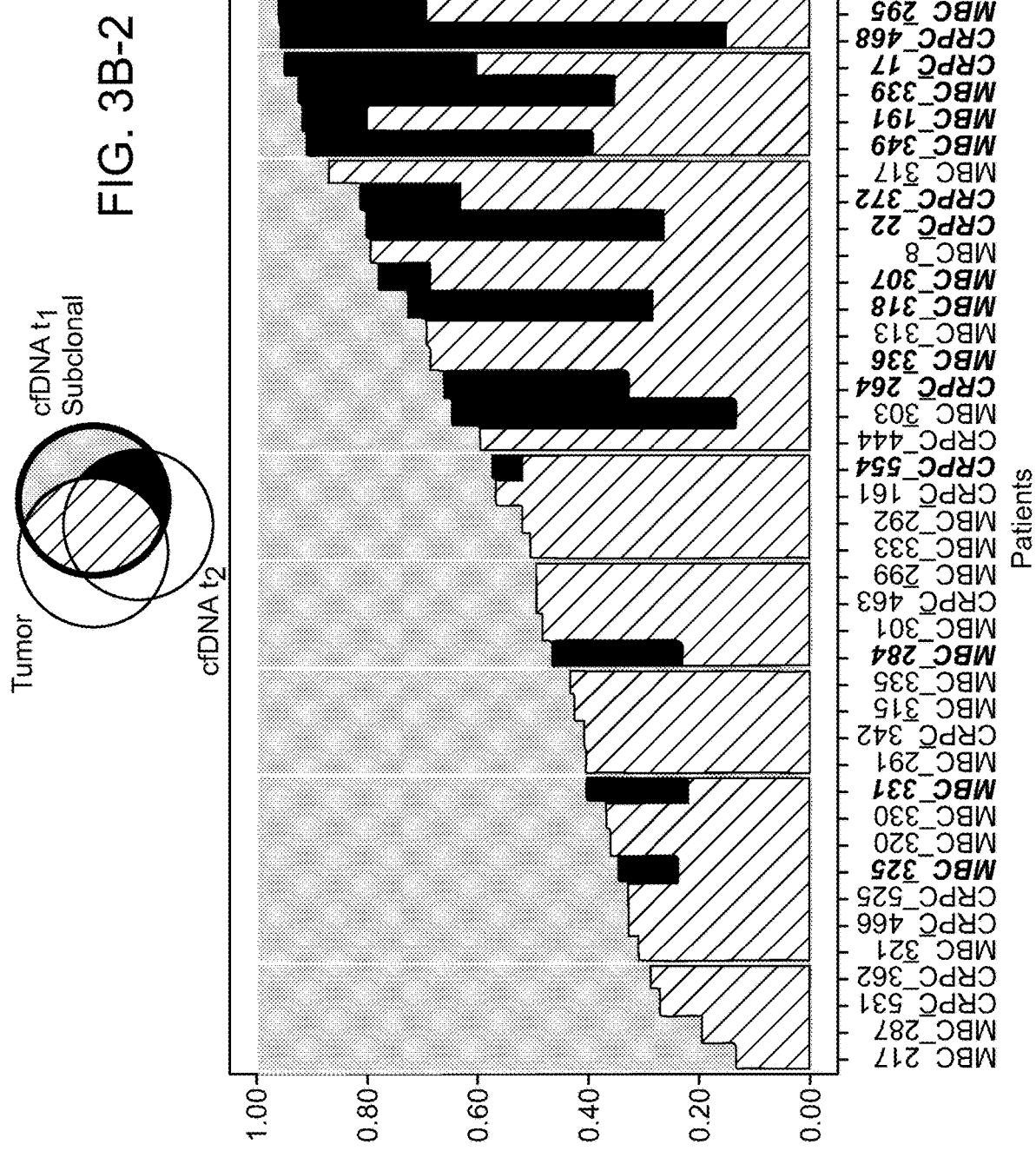

ULP-WGS of cfDNA can be Used for Comprehensive Genomic Characterization of a Tumor Biopsy The overlap of SSNVs and SCNAs between whole-exome sequencing of cfDNA and matched tumor biopsies was examined. Clonal and subclonal events were distinguished by estimating the proportion of an observed somatic event out of the total tumor-derived DNA (cancer cell fraction, hereafter CCF) using ABSOLUTE (Carter et al. Nat. Biotechnol. 30, 413-421 (2012)). On average, 88% of the clonal (CCF≥0.9; range 29-100%) and 47% of the subclonal (CCF<0.9; range 9-100%) SSNVs that were detected in the tumor were confirmed to be present in cfDNA (i.e. supported by ≥3 variant reads) (FIG. 3A). Similarly, for SSNVs detected in the cfDNA, on average, 88% of the clonal (range 33-100%) and 45% of the subclonal (range 14-88%) SSNVs were confirmed in the tumor (FIG. 3B). For eighteen patients, blood was collected at a second time point ($t_2$, two to six weeks later) and WES of cfDNA was performed. On average, 56% of the subclonal SSNVs that were detected in the earlier cfDNA sample ($t_1$) were not confirmed in the tumor biopsy (FIG. 3B). The confirmation of these cfDNA-exclusive events supports the possibility that these alterations may be derived from unprofiled tumor clones that were not captured by the core biopsy of a single lesion. Similar results were observed for SCNA events of various sizes detected in the tumor (average 80% clonal, 77% subclonal confirmed in cfDNA) and detected in cfDNA (average 76% clonal, 70% subclonal confirmed in tumor). Without being bound by theory, these findings indicate that cfDNA offers a suitable proxy for comprehensive genomic characterization of a tumor biopsy and may not derive solely from the single biopsied lesion.

Figure 3C:
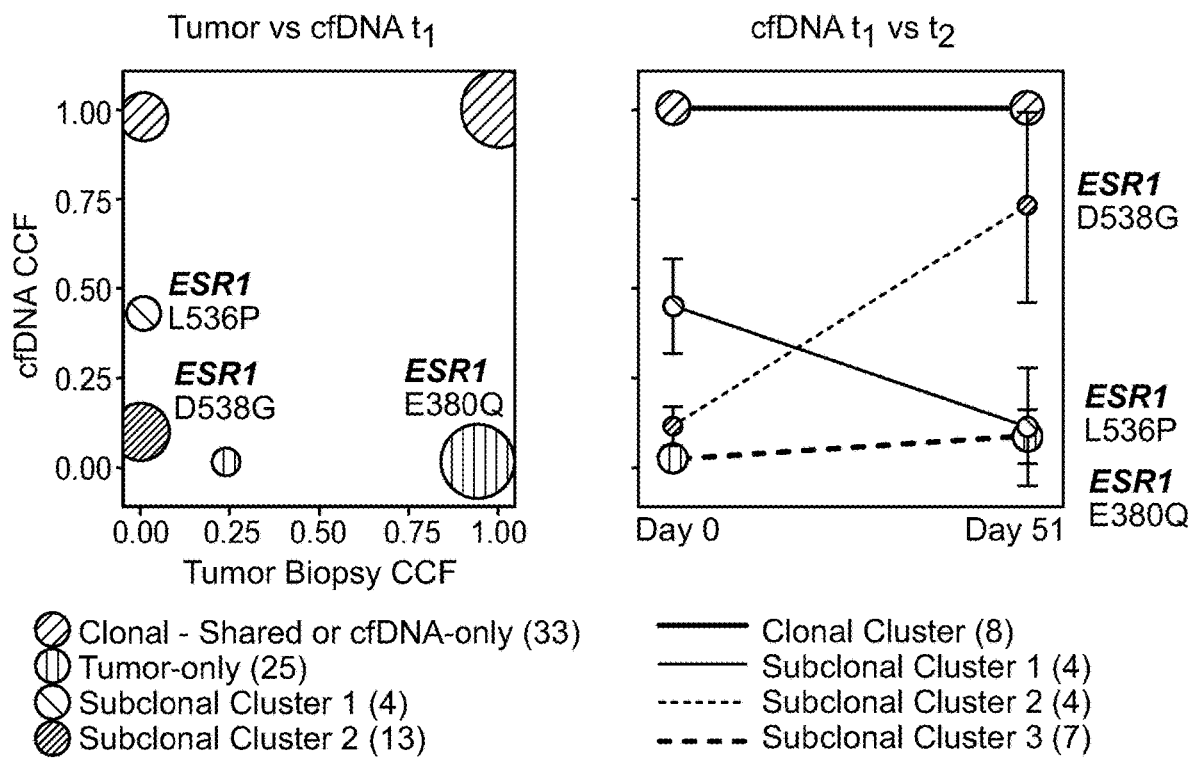
Figure 3C:
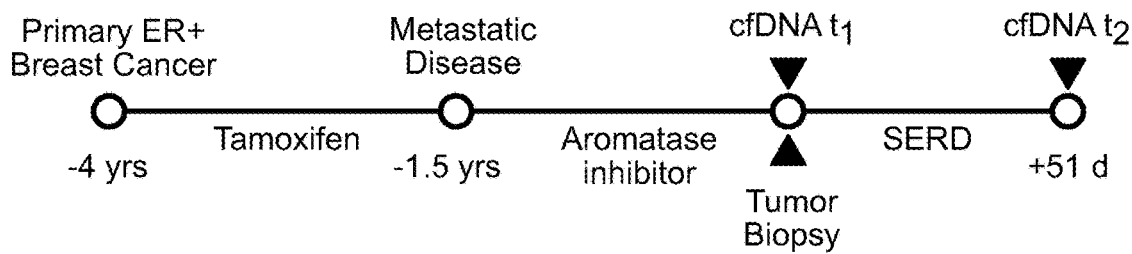

Between cfDNA and the metastatic lesions, a median of 46% (range 12%-100%) of SSNVs and 78% (range 25-95%) of genes altered by SCNAs were observed to be clonal (CCF≥0.9) in both samples. For seventeen of the patients with a second cfDNA sample, clonal stability was observed, with the majority (>50%) of SSNVs having similar clonality (±0.1 CCF) between time points. Distinct subclonal patterns of SSNVs was also observed, including evolving clonal dynamics. For instance, in a metastatic breast cancer patient (MBC_284) previously treated with an aromatase inhibitor, multiple mutations were detected in ESR1 (D538G and L536P) in cfDNA at $t_1$ (0.12 and 0.45 CCF) (FIG. 3C). Interestingly, the clonal fractions of these mutations were inverted at $t_2$ (0.73 and 0.12, respectively) after 51 days of treatment with a selective estrogen receptor degrader (SERD). Without being bound by theory, this indicates that these ESR1 mutations may have different sensitivities to SERDs. An ESR1 mutation (E380Q) was also detected in the tumor biopsy that was confirmed at low clonal fractions in cfDNA. These clonal shifts in resistance-associated mutations suggest that longitudinal analysis of whole-exome sequencing of cfDNA may nominate potential mechanisms of resistance to therapy.

Example 4

ULP-WGS of cfDNA Identified Focal Copy Number Alterations (CNAs) with Comparable Performance to Whole Exome Sequencing of the Same Library or Matched Tumor Biopsy To determine whether the data obtained through ULP-WGS may be used to reveal genomic aberrations in tumor tissue, a comparison study was conducted (FIGS. 2A-2D). Focal copy number aberrations (CNAs) identified based on ULP-WGS of cfDNA were compared to focal CNAs obtained through whole-exome sequencing of the same library (FIG. 2A, middle panel) and focal CNAs obtained using whole-exome sequencing of a matched tumor biopsy. Importantly, focal CNAs detected using ULP-WGS were concordant with higher depth, whole-exome sequencing of the same library (technical validation) and were also concordant with whole-exome sequencing of a matched tumor biopsy (biological comparison).

Figure 4B:
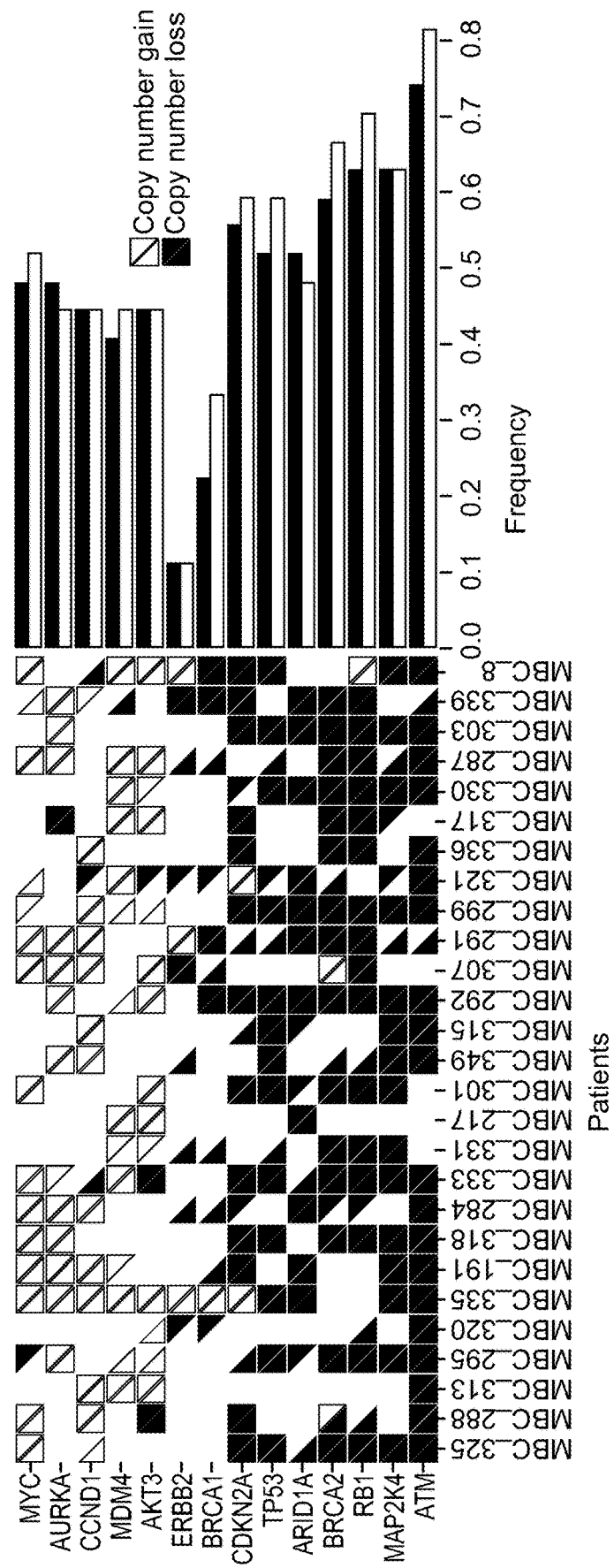

Whether whole-exome sequencing of cfDNA can serve as a proxy for tumor biopsies in multiple applications of cancer exome analyses was assessed. First, known cancer-associated somatic alterations (Van Allen et al. Nat. Med. 20, 682-688 (2014)) between cfDNA and tumor biopsies was compared for 27 metastatic breast and 14 metastatic prostate cancer patients. In breast cancer, similar frequencies of altered genes (Pearson's r=0.97) were observed in both cfDNA and tumor biopsies, including mutations in TP53, ESR1, and PIK3CA, amplification of MYC, CCND1, ERBB2, PIK3CA, and losses of ATM and RB1 (FIG. 4A). Similarly, in prostate cancer, frequent amplifications of AR were observed, as well as mutations and LOH of TP53. Next, to discover statistically significant genes recurrently mutated above background rates, MutSig2CV Lawrence et al. Nature 499, 214-218 (2013); Lawrence et al. Nature 505, 495-501 (2014)) was applied independently to cfDNA and tumor biopsies and ESR1, TP53, PIK3CA, ARID1A were identified (FIG. 4A). Among these mutated genes, a statistically significant enrichment of non-silent mutations was found in ESR1 and ARID1A for both cfDNA and tumor biopsies in 20 ER+/HER2− metastatic cancer patients when compared to 279 primary ER+/HER2− breast carcinomas published previously by The Cancer Genome Atlas (TCGA) (Ciriello et al. Cell 163, 506-519 (2015)) (Bonferroni corrected Fisher's exact test p=$1.46 \times 10^{-8}$ and $2.58 \times 10^{-2}$ respectively). The metastatic breast cancer biopsies in this study are derived from a larger cohort in which ARID1A was found to be significantly mutated and enriched with respect to TCGA (Cohen et al. SABCS 2016). The mutational enrichment was significant in both metastatic biopsies and cfDNA, suggesting that cfDNA exome sequencing can lead to similar biological insights as tumor biopsies and may enable genomic discovery from larger cohorts.

Figure 4D:
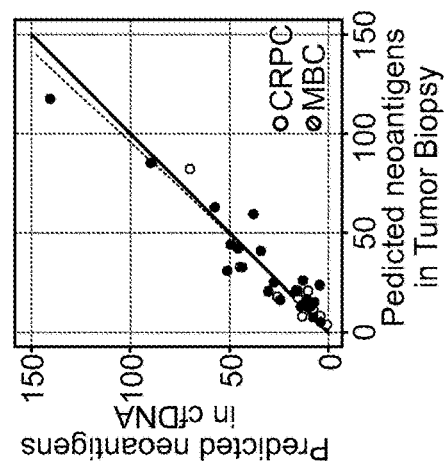
Figure 4C:
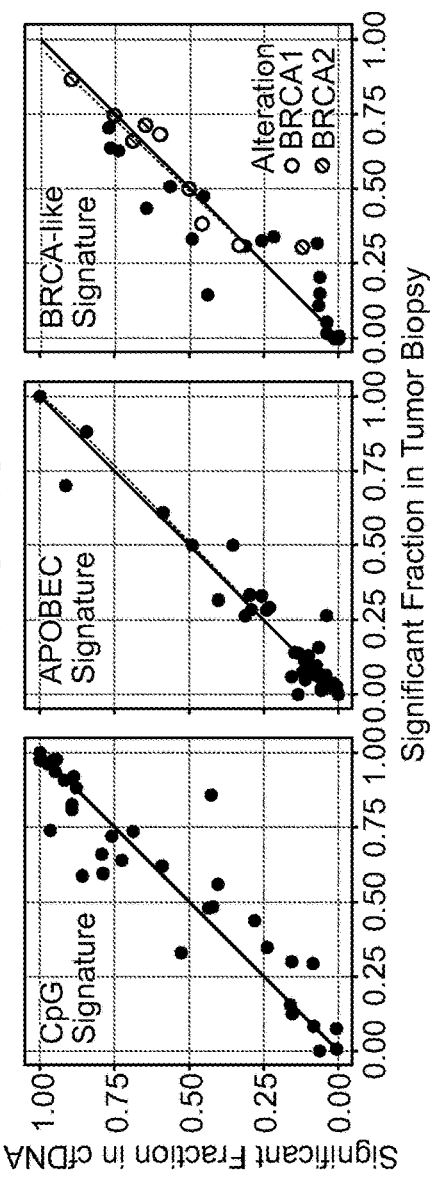

As mutational processes operating in tumors have been associated with potential sensitivity to specific therapies (Alexandrov et al. *Nat. Commun.* 6, 8683 (2015)) and their detection in cfDNA could be clinically significant, the mutational signatures (Kasar et al. *Nat. Commun.* 6, 8866 (2015); Kim et al. *Nat. Genet.* 48, 600-606 (2016)) present in cfDNA and tumor biopsy were analyzed. Three previously (Alexandrov et al. *Nature* 500, 415-421 (2013)) described mutational signatures associated with aging (C>T mutations at CpG dinucleotides), APOBEC activity (C>T or C>G at a TC[A/T] context), and DNA homologous recombination deficiency (BRCA-like (Alexandrov et al. *Nat. Commun.* 6, 8683 (2015))) were identified (FIG. 4C). The predicted fraction of mutations belonging to each signature was highly concordant between cfDNA and tumor biopsies (adjusted $R^2$=0.92, $p<1\times10^{-16}$, FIG. 4C). Patients with predicted homozygous loss of BRCA1 or BRCA2 had higher BRCA-like signature activity in both cfDNA and tumor biopsies (Wilcoxon rank-sum test, one-tailed, $p<0.01$). Without being bound by theory, these results indicated the analysis of cfDNA to be a complementary approach to predict homologous recombination deficiency and could provide information regarding potential sensitivity to drugs, such as PARP inhibitors (Mateo et al. *N. Engl. J. Med.* 373, 1697-1708 (2015)) that target this pathway.

As cancer immunotherapies have been effective in clinical trials and analysis of neoantigens may influence treatment strategies (Rizvi et al. *Science* 348, 124-128 (2015)), the number of somatic mutations that were predicted to be neoantigens in cfDNA and matched tumor biopsies were compared. The binding affinity of missense SNVs to patient-specific MHC Class I alleles inferred from germline whole-exome sequencing data (Nielsen et al. *PLoS One* 2, (2007); Hoof et al. *Immunogenetics* 61, 1-13 (2009); Shukla et al. *Nat. Biotechnol.* 33, 1152-1158 (2015)) was predicted. Any mutation with an $IC_{50}<500$ nM was considered a predicted neoantigen. The number of predicted neoantigens was strongly correlated between cfDNA and tumor biopsies (adjusted $R^2$=0.90, $p<1\times10^{-16}$). Without being bound by theory this indicates that whole-exome sequencing of cfDNA could lead to similar prediction of potential tumor immunogenicity as would sequencing of tumor biopsies (FIG. 4D).

Figure 4E:
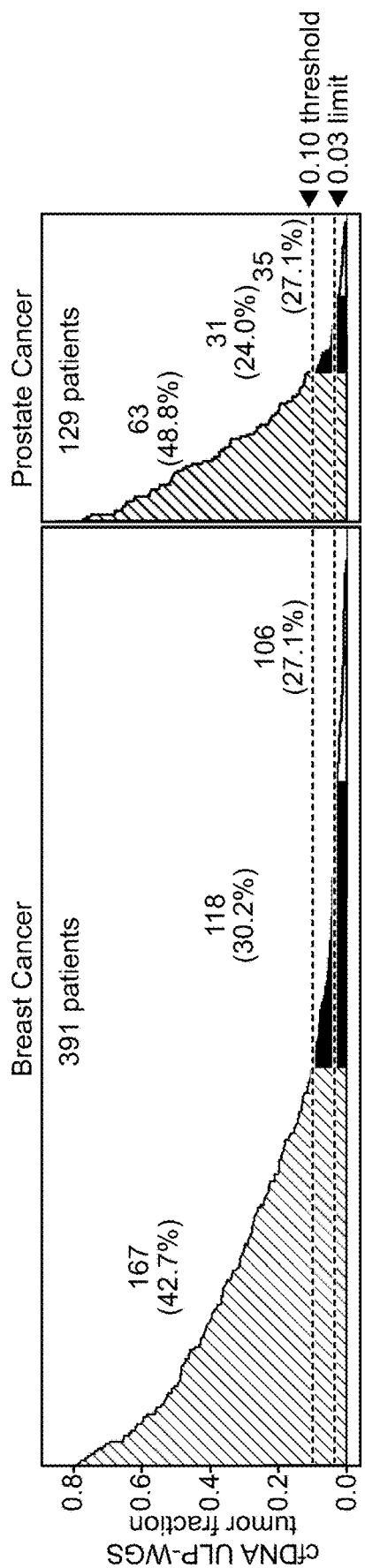

Finally, these results indicate that many patients with metastatic cancer will have sufficient tumor-derived cfDNA for whole-exome sequencing. ULP-WGS of cfDNA was analyzed from 913 blood samples from 391 patients with metastatic breast cancer and 579 blood samples from 129 patients with metastatic prostate cancer (FIG. 4E). Overall, 73% of patients with breast and prostate cancer, had detectable (≥0.03) tumor-derived cfDNA. Additionally, 43% and 49% of breast and prostate cancer patients, respectively, had sufficient tumor fraction (Cibulskis et al. *Nat. Biotechnol.* 31, 213-219 (2013); Carter et al. *Nat. Biotechnol.* 30, 413-421 (2012)) (≥0.1) for standard whole-exome sequencing in at least one blood sample.

Figure 5A:
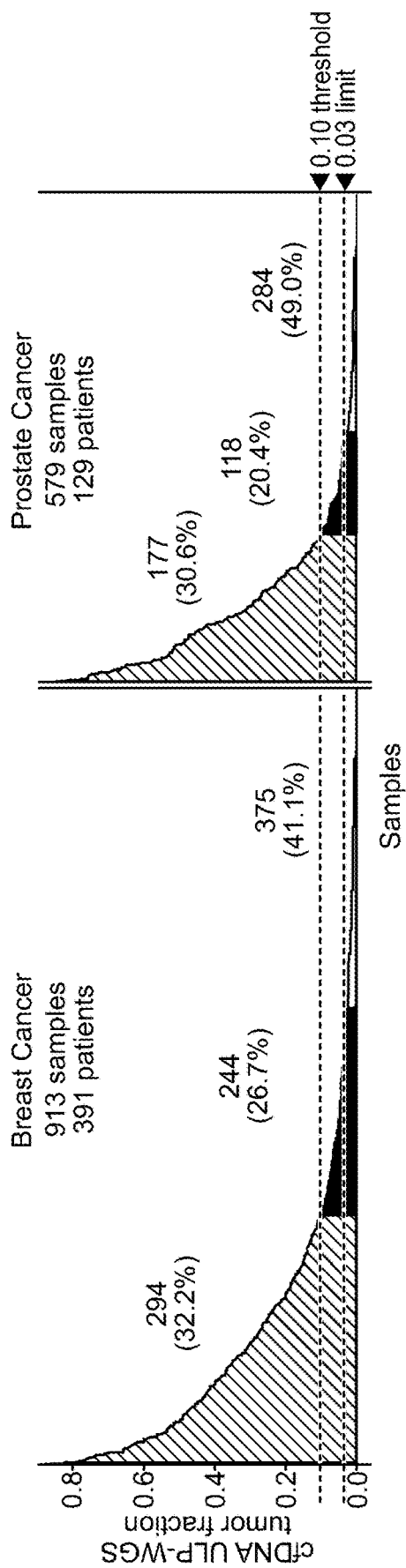
Figure 5C:
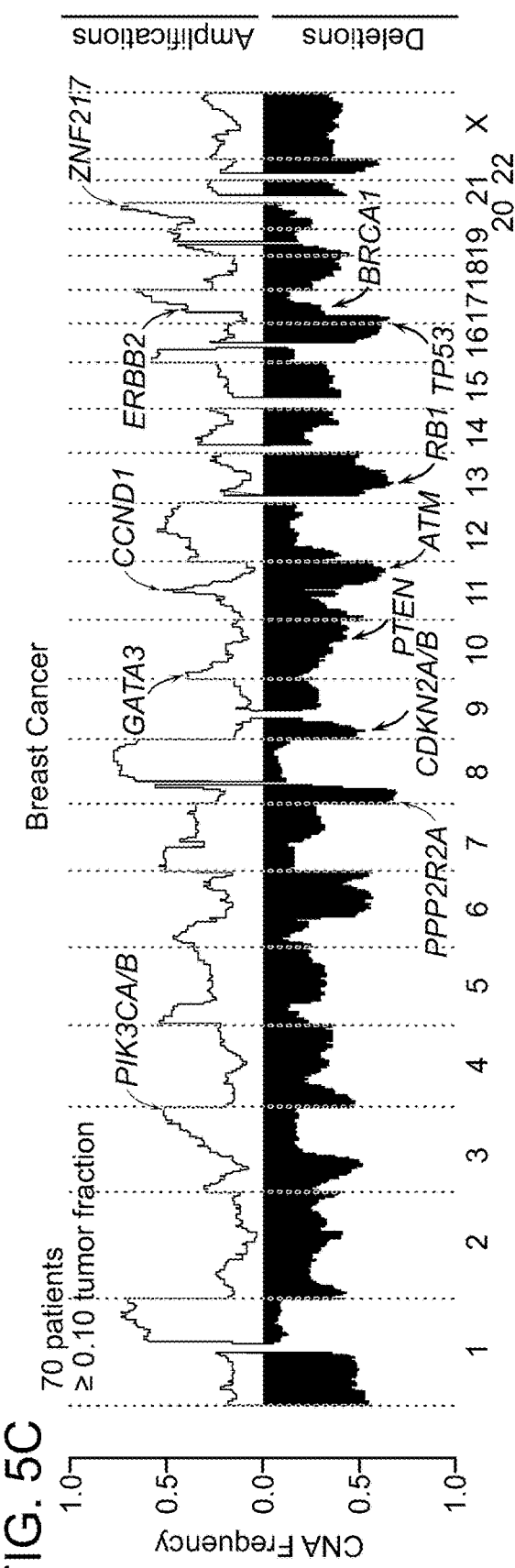
Figure 5D:
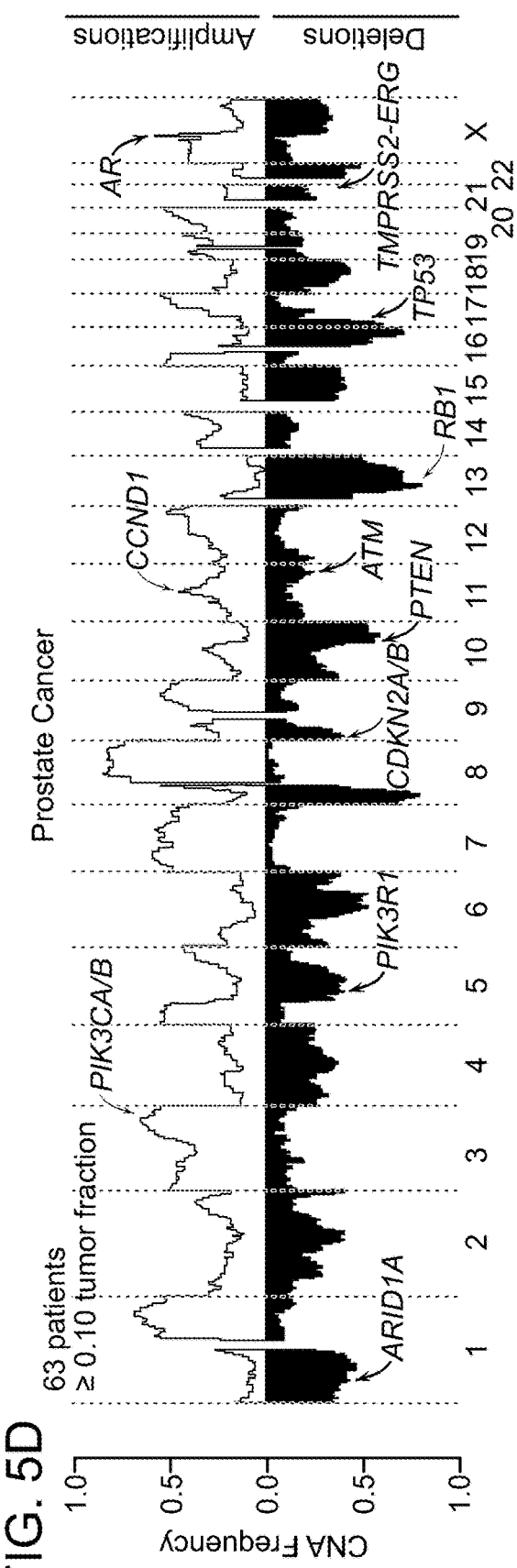
Figure 6E:
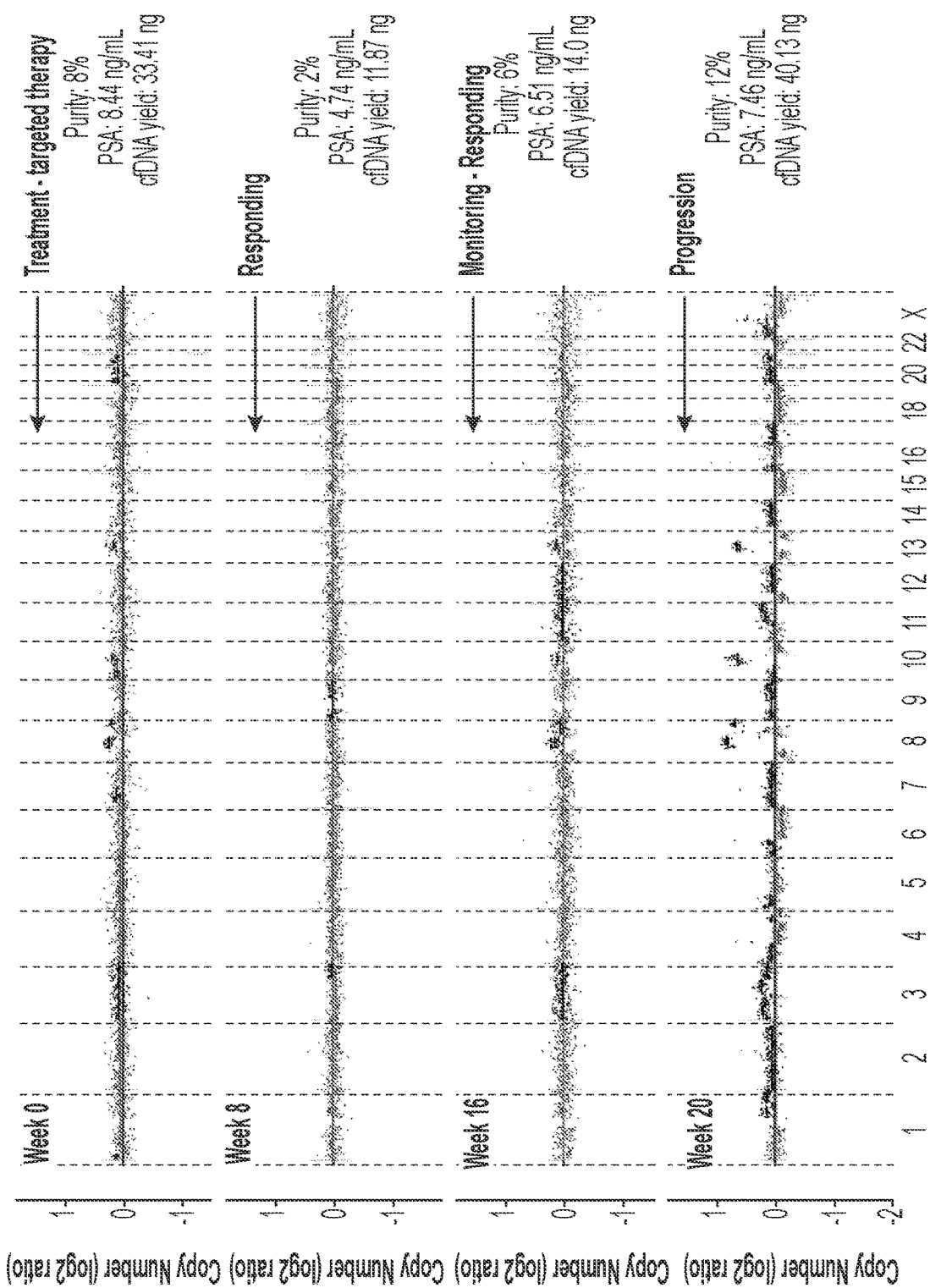

Subsequent analysis of SCNAs detected from ULP-WGS of these samples revealed SCNA landscapes that closely reflected those reported (Curtis et al. *Nature* 486, 346-352 (2012)), including biopsies of metastatic tumors from 150 patients with castration-resistant prostate cancer (Robinson et al. *Cell* 161, 1215-1228 (2015)) (FIGS. 5A, 5B, 5D). Frequent alterations of known tumor suppressor genes (e.g. ATM, RB1, TP53, CDKN2A/B, PTEN, PPP2R2A) and oncogenes (e.g., CCND1, AKT1, GATA3, ERBB2, PIK3CA, AR) (Curtis et al. *Nature* 486, 346-352 (2012); Robinson et al. *Cell* 161, 1215-1228 (2015); Cancer Genome Atlas Network. *Nature* 490, 61-70 (2012)) were also identified. These results demonstrate that whole-exome sequencing is possible in a substantial fraction of patients with metastatic breast and prostate cancers. Furthermore, using the estimated tumor fraction can help to calibrate the required sequencing depths for lower tumor content samples.

Example 5

Focal CNAs Landscape Based on ULP-WGS of cfDNA are Similar to the Copy Number Landscapes Generated Using Conventional Methods ULP-WGS was used to map focal copy number aberrations (CNAs) present in cell free DNA isolated from blood samples obtained from 43 patients with metastatic castration resistant prostate cancer. In each patient, the purity of tumor cell-free DNA was greater than 10% and the coverage of the genome was greater than 0.05×. Results obtained using ULP-WGS were compared to copy number landscapes generated using whole-exome sequencing of over a hundred metastatic tumor biopsies (FIGS. 5A-5D; Robinson et al. *Cell* 161, 1215-1228 (2015)). Importantly, ULP-WGS generated essentially the same copy number profile as was obtained by Robinson et al. but at a significant cost savings. ULP-WGS on cfDNA isolated from blood cost just $860 (43 samples×$20 worth of sequencing per sample). In comparison, the methods used by Robinson et al., required a needle biopsy, pathologist review, and 150× whole-exome sequencing.

Example 6

ULP-WGS of cfDNA can be Used to Characterize and Monitor a Patient's Response to Therapy CNAs landscape derived from ULP-WGS of cfDNA were used to determine whether a subject with prostate cancer responded to treatment (FIGS. 6A-6E). ULP-WGS was used to characterize CNAs present in cfDNA isolated from blood samples obtained from prostate cancer patients over time. Serially sampled blood from patients on therapy revealed correlations in tumor fractions with clinical response. This suggests that measuring tumor fractions in cell-free DNA using ULP-WGS offers an early readout of clinical response.

Results described herein above were obtained using the following methods and materials.

CfDNA Isolation, Library Construction, and Sequence Data Generation

CfDNA extractions were carried out using commercially available automated DNA sample preparation technology from Qiagen, QiaSymphony®. The extracted DNA was quantified using commercially available DNA quantification assay, PicoGreen® assay. Sequencing libraries were constructed by direct ligation of adapters using Kapa HyperPrep kit from KapaBiosystems. One library was constructed for each patient. A small fraction (~1%) of each barcoded library was pooled and submit for 1 lane of HiSeq2500 per 96 samples. The sequence "barcode" allowed the library to be associated with the patient from which it was derived.

High throughput DNA sequencing of the DNA fragments in each library was carried out using commercially available sequencing technology SBS (sequencing by synthesis) by Illumina on commercially available system, HiSeq 2500 from Illumina.

Following analysis of tumor fractions, the remainder of the library was used to perform pooled hybrid capture using the Illumina Rapid Capture protocol using Illumina's baits for the whole-exome. Each library was sequenced to standard exome depths. In parallel, whole-exome sequencing of germline DNA extracted from bulk white blood cells was carried out using conventional methods (Illumina Rapid Capture)

Copy Number Analysis

Cell-free DNA samples were initially qualified for whole exome sequencing (WES) using ultra-low-pass whole genome sequencing (ULP-WGS). The ULP-WGS is a low cost approach to nominate samples containing sufficient fraction of tumor-derived DNA for whole exome sequencing.

Large numbers of cell-free DNA samples were sequenced to an average of 0.1× genome-wide sequencing coverage. Samples with fewer than 1,500,000 reads (0.05×) were excluded due to insufficient coverage for analysis. A statistical approach (available from HMMcopy software) was used to correct for GC-content and mappability (sequence uniqueness) biases in read counts within genomic bins of 1 Mb, which substantially improves signal to noise ratio. Next, a modified approach was developed based on the TITAN framework as described by Ha et al. Genome Res. 22, 1995-2007 (2012); and Ha, et al. Genome Res. 24, 1881-1893 (2014). This approach performs segmentation of the count data, copy number prediction, and tumor fraction and ploidy estimation. This approach was optimized for increased sensitivity to detect events from low amounts of tumor-derived DNA in the absence of a control sample. Benchmarking of the tumor fraction estimates was carried out using simulation of tumor-normal mixing and comparison to corresponding whole exome sequencing data, revealing a robust lower estimation level of tumor content.

Analysis of ULP-WGS Using ichorCNA

In order to access the quality and presence of detectable tumor, ULP-WGS of cfDNA was performed to an average genome-wide fold coverage of 0.1×. The depth of coverage in a ULP sample was analyzed to evaluate large-scale copy number alterations (CNAs) and aneuploidies. A probabilistic model was developed and a software package implemented called "ichorCNA," which uses concepts from existing algorithms (Ha et al. *Genome Res.* 24, 1881-1893 (2014); Ha et al. *Genome Res.* 22, 1995-2007 (2012)) designed for deep coverage WGS/WES data to simultaneously predict regions of CNAs and estimate the fraction of tumor in ULP-WGS. The workflow consisted of 3 steps: 1) Computing read coverage, 2) Data normalization, and 3) CNA prediction and estimation of tumor fraction.

Read Coverage Data

The genome is divided into T non-overlapping windows, or bins, of 1 Mb. Aligned reads are counted based on overlap within each bin. This was done using the tools in HMMcopy Suite (http://compbio.bccrc.ca/software/hmmcopy/). Centromeres are filtered based on chromosome gap coordinates obtained from UCSC for hg19, including one 1 Mb bin up- and downstream of the gap. The short fragment sizes of cfDNA (e.g., 166 bp) often contain overlapping paired reads for 100 bp read lengths and can lead to two overlapping reads representing a single fragment. Abundance of cfDNA fragments has been shown to exhibit tissue-specific differences along local ~200 bp scale regions of the genome (Snyder et al. *Cell* 164, 57-68 (2016)). For this analysis, because read counts are computed for large bins, the double-counting at ~200 bp scale is not likely to have a major effect. To determine copy number alterations and structural rearrangements at 500 bp or smaller scales, then switching to counting read coverage of fragments, rather than reads, will be more appropriate.

Data Normalization

The read counts are then normalized to correct for GC-content and mappability biases using HMMcopy R package (Ha et al. *Genome Res.* 22, 1995-2007 (2012)). Briefly, two LOESS regression curve-fitting are performed to the bin-wise 1) GC-fraction and read counts, followed by 2) mappability uniqueness score and read counts. The curvefitting was only applied to autosomes. This generates corrected read counts $r_t$ for each bin $t \in \{1, \ldots, T\}$.

Next, the gender of the patient is determined by inspecting the corrected read counts in chromosome X and Y. There are two criteria to determine if the sample is a male (otherwise the sample is a female):

1. The proportion of uncorrected chrY read counts out of the total number of reads is >0.001 and
2. The median corrected log ratio of chrX is <−0.5.

If the sample is a male, then the bins in chrX are re-scaled, $r_t \in \text{chrX}/\text{median} (r_t \in \text{chrX})$.

ULP-WGS was also performed on cfDNA from 27 healthy donors using the same protocol in order to create a reference dataset. These data help to further normalize the cancer patient cfDNA to correct for systematic biases arising from library construction, sequencing platform, and cfDNA-specific artifacts. The healthy donor cfDNA ULP data were processed as above and also corrected for GC-content and mappability biases as above. This generated corrected read counts hit for each bin $t \in \{1, \ldots, T\}$ and each donor sample i. Then, the median at each bin was computed across the 27 samples to generate a reference dataset, $h_{1:T}$.

For a given cancer patient cfDNA sample and each bin t, the $\log_2$ copy ratios are computed as $$\log_2 = \left(\frac{r_t}{h_t}\right).$$

ichorCNA: Copy Number Prediction and Tumor Fraction Estimation Using a HMM

Representation of tumor-normal clonality admixture The cancer patient cfDNA CNA signals is composed of an admixture between DNA fragments derived from tumor and non-tumor cells. A 2-component mixture was used to model this explicitly (Carter et al. *Nat. Biotechnol.* 30, 413-421 (2012); Ha et al. *Genome Res.* 24, 1881-1893 (2014); Ha et al. *Genome Res.* 22, 1995-2007 (2012); Van Loo et al., *Proc Natl Acad Sci USA* 107, 1-6 (2010); Yau et al., *Genome Biology* 11, R92 (2010))

observed CNA$\propto 2n+(1-n)c$ where n is the non-tumor proportion, (1−n) is the tumor proportion, and c is the copy number for a specific alteration (e.g. 1 for deletion, 3 for gain, etc.).

For subclonal events, a third component is used to represent DNA fragments derived from tumor cells not harboring the CNA event (Carter et al. *Nat. Biotechnol.* 30, 413-421 (2012); Ha et al. *Genome Res.* 24, 1881-1893 (2014); Yau et al., *Genome Biology* 11, R92 (2010)), observed CNA$\propto 2n+2s(1-n)+(1-s)(1-n)c$ (Equation 1)

where s is the proportion of tumor not containing the event with c copy number. Thus, (1−s) is similar to the definitions of tumor-cellular-prevalence (Ha et al. *Genome Res.* 24, 1881-1893 (2014)) or cancer-cell-fraction or tissue tumors (Carter et al. *Nat. Biotechnol.* 30, 413-421 (2012).

State space The number of copy number states is dynamic depending on the initial average tumor ploidy $\phi \in \{2, 3, 4\}$.

$$K = \begin{cases} \{1, 2, 3, 4, 5\} & \phi = 2 \\ \{1, 2, 3, 4, 5, 6\} & \phi = 3 \\ \{1, 2, 3, 4, 5, 6, 7\} & \phi = 4 \end{cases}$$

The copy number states are mapped to hemizygous deletions (HETD, 1), copy neutral (NEUT, 2), copy gain (GAIN, 3), amplification (AMP, 4), and high-level amplification (HLAMP, 5-7 copies). The homozygous deletions state (HOMD, 0 copies) is excluded. For the analysis performed in this study, the copy number was fixed to be $K=\{1, 2, 3, 4, 5\}$ for all ploidy initializations.

For subclonal events, two additional states are included: subclonal hemizygous deletion (HETD$_{sc}$) and subclonal copy gain (GAIN$_{sc}$).

$$K = \{K, \{1,3\}_{SC}\}$$

A copy number state is assigned to $G_t$ for each bin t and the initial distribution of these copy number states is given by $G_0 \sim \text{Mult}(\pi)$.

Emission model The input log copy ratios $l_{1:T}$ is modeled using a Student's-t distribution with $\mu_g$, $\lambda_g$, and $v_g$ are the mean, precision, and degrees of freedom, conditional on copy number state $g \in K$ at bin t, $$p(l_t|G_t=g)=St(l_t|\mu_g, \lambda_g, v_g)$$

Mean $\mu_g$ is defined by the 3-component mixture (Equation 1) for copy number state g with unknown global parameters n and average tumor ploidy $\phi$, $$\mu_g = \log\left(\frac{2n + 2s(1-n) + (1-s)(1-n)c_g}{2n + (1-n)\phi}\right)$$

Precision $\lambda_g$ for each $g \in K$ are also model parameters. The degrees of freedom $v_g$ is a constant (2.1) and is not estimated.

Transition model A stationary (homogeneous) transition model is used in the HMM. Because all bins have equal sized intervals, with the exception of centromere regions, a non-stationary transition model to account for varying genomic distances between data points was not used. The transition matrix containing the transition probabilities is given by $$p(G_t = j | G_{t-1} = i) = A_{ij}$$

$$A_{ij} = \begin{cases} e & i = j \\ \frac{1-e}{|K|-1} & \text{otherwise} \end{cases}$$

where e is set to 0.99999.

Prior model The HMM is implemented as a Bayesian framework with priors for each model parameter: Student's-t parameters $\mu_g$, $\lambda_g$ for each $g \in K$, transition probabilities A, initial state distribution $\pi$, and global parameters n, s, and $\phi$, $n \sim \text{Beta}(\alpha_n, \beta_n)$
$s \sim \text{Beta}(\alpha_s, \beta_s)$
$\phi \sim \text{Gamma}(\alpha_\phi, \beta_\phi)$
$\lambda_g \sim \text{Gamma}(\alpha_g, \beta_g)$
$A \sim \text{Dir}(\delta_A)$
$\pi \sim \text{Dir}(\delta_{pi})$ where $\psi = \{\delta_A, \delta_\pi, \alpha_g, \beta_g, \alpha_n, \beta_n, \alpha_s, \beta_s, \alpha_\phi, \beta_\phi\}$ for all $g \in K$ are the hyper-parameters.

Learning and inference The model parameters $\theta = \{\mu 1:|K|, \lambda 1:|K|, A, \pi, n, \phi\}$ are estimated using the expectation-maximization (EM) algorithm given the data $D=\{l_{1:T}\}$. In the E-step, we applied the forwards-backwards algorithm to compute the posterior probabilities, $p(G_t=g|D, \theta)$. In the M-step, the parameters $\theta(n)$ at EM iteration n are estimated using the maximum a posteriori (MAP) estimate.

$$\theta^{(n)} = \underset{\theta}{\text{argmax}}\{p(G | D, \theta^{(n-1)})p(D, G | \theta^{(n)})\}$$

The converged parameters $\hat{\theta}$ is determined by the EM convergence criteria such that the change the complete-data log-likelihood (including priors) $F(n)=\log p(D, Z|\theta(n-1))+ \log p(\theta(n)|\psi)$ changes less than 0.1% $(F(n)-F(n-1)<0.001)$. The complete-data log-likelihood at convergence is denoted $\hat{F}$.

The Viterbi algorithm is then applied to find the optimal copy number state path for all bins, $$\hat{G}_{1:T} = \underset{G}{\text{argmax}}\, p(G_{1:T} | D, \hat{\theta})$$

Chromosome 19 was excluded during parameter estimation (i.e., EM) due to systematic decrease in log$_2$ copy ratio values across majority of samples for bins within chr19 after GC-content correction. As a result, the estimation of tumor fraction is not influenced by this systematic bias. However, chr19 was included in the Viterbi algorithm as part of generating a genome-wide solution.

Model selection In order to avoid the local optimal limitation of EM, multiple restarts are performed by performing EM over a range of initializations for tumor fraction $(n^{(0)} \in \{0.35, 0.45, 0.50, 0.65, 0.75, 0.85, 0.95\})$ and tumor ploidy $(\varphi^{(0)} \in \{2, 3, 4\})$ parameters. The solution with the maximum complete-data log-likelihood over each initialization pair, $(n^{(0)}, \varphi^{(0)})$ is chosen.

Due to the problem of identifiability between clonal and subclonal events, which is especially challenging in ULP sequencing and the absence of allelic information, solutions with >50% of the genome harboring subclonal CNA or >70% of CNA calls being subclonal are not selected.

Solutions with a total alteration fraction (based on bins) <0.05 and having the largest CNA event be <50 bins are reassigned a tumor fraction of zero.

Post-analysis correction For better comparability between samples with varying tumor fractions, the segment median log ratio values are corrected to account for the tumor fraction of the sample. That is, for lower tumor fraction samples, the log ratio values will be adjusted higher signals. Given the previous definition of the emission model (Equation 2), the tumor-content-corrected log2 copy ratios r̂t at bin t from the observed $\log_2$ copy ratio $l_t$ and estimated normal content (n) or tumor fraction (1−n), $$S = 2n + (1-n)\phi$$
$$c = \frac{2^{l_t}S - 2n}{(1-n)}$$
$$\hat{r}_t = \log_2\left(\frac{c}{\phi}\right)$$

If $$\frac{c}{\phi}$$

is negative, the it is set to $2\times10^{-9}$ prior to log transformation. Run-time and complexity The ichorCNA HMM component has O (KT) in memory and O (K²T) in time. The run-time of the algorithm for 0.1× coverage is 1 minute for read coverage computation and 1 minute for analysis using the HMM.

Other Embodiments

From the foregoing description, it will be apparent that variations and modifications may be made to this invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of characterizing DNA in a biological sample comprising or suspected of comprising tumor-derived DNA, the method comprising:
   (a) isolating fragments of DNA from a biological sample;
   (b) constructing an unamplified DNA library comprising said fragments, wherein the library is constructed using from about 2 ng to about 85 ng of DNA;
   (c) obtaining sequence data by sequencing the library to about 0.01-5× genome- or exome-wide sequencing coverage;
   (d) generating a copy number alteration profile for the sequence data; and
   (e) using the copy number alteration profile to detect presence or absence of a chromosomal copy number alteration in the sequence data, wherein detection of a chromosomal copy number alteration indicates that at least a portion of the DNA in the sample was derived from a neoplastic cell and failure to detect such an alteration indicates that DNA present in the sample is not derived from a neoplastic cell.

2. A method of characterizing DNA in a biological sample, the method comprising:
   (a) isolating fragments of DNA from a biological sample;
   (b) constructing an unamplified DNA library comprising said fragments, wherein the library is constructed using from about 2 ng to about 85 ng of DNA;
   (c) obtaining sequence data by sequencing the library to about 0.01-5× genome- or exome-wide sequencing coverage;
   (d) generating a copy number alteration profile for the sequence data, wherein generating the copy number alteration profile comprises computing sequence read coverage and sequence data normalization; and
   (e) using the copy number alteration profile to detect presence or absence of a chromosomal copy number alteration or focal chromosomal copy number alteration in the sequence data.

3. A method of determining the purity of tumor-derived DNA in a sample, the method comprising:
   (a) isolating fragments of DNA from a biological sample;
   (b) constructing an unamplified DNA library comprising said fragments, wherein the library is constructed using from about 2 ng to about 85 ng of DNA;
   (c) obtaining sequence data by sequencing the library to at least about 0.1X genome- or exome-wide sequencing coverage;
   (d) generating a copy number alteration profile for the sequence data;
   (e) using the copy number alteration profile to detect the presence or absence of a chromosomal copy number alteration in the sequence data; and
   (f) analyzing any chromosomal copy number alteration(s) detected in the sample to determine the purity of tumor-derived DNA in the sample.

4. The method of claim 3, further comprising (g) carrying out whole exome sequencing.

5. The method of claim 2, wherein the focal chromosomal copy number alteration is selected from the group consisting of about 1 KB, 3 KB, 5 KB, 10 kb, 50 kb, 100 kb, 500 kb, 2 MB, 3 MB, 4 MB, 5 MB, 10 MB, 50 MB, and 100 MB of DNA.

6. The method of claim 1, wherein the biological sample is tissue sample or a liquid biological sample selected from the group consisting of blood, plasma, serum, cerebrospinal fluid, phlegm, saliva, urine, semen, prostate fluid, breast milk, and tears.

7. The method of claim 1, wherein the sample is derived from a subject having or suspected of having a neoplasia.

8. The method of claim 1, wherein the sample is a fresh or archival sample derived from a subject having a cancer selected from the group consisting of prostate cancer, metastatic prostate cancer, breast cancer, triple negative breast cancer, lung cancer, colon cancer, or any other cancer comprising aneuploid cells.

9. A method of identifying a subject as having a neoplasia or monitoring disease status, the method comprising:
   (a) isolating fragments of cell-free DNA from a biological sample derived from the subject;
   (b) constructing an unamplified, cell-free DNA library comprising said fragments, wherein the library is constructed using from about 2 ng to about 85 ng of DNA;
   (c) obtaining sequence data by sequencing the library to at least about 0.01-5× exome- or genome-wide sequencing coverage;
   (d) generating a copy number alteration profile for the sequence data, and
   (e) using the copy number alteration profile to detect the presence or absence of a chromosomal copy number alteration in the sequence data, wherein the presence of a chromosomal copy number alteration identifies the subject as having a neoplasia, and the absence of a chromosomal copy number alteration indicates that no neoplasia was detected in the sample from the subject and, optionally, comparing the chromosomal copy number alteration(s) in the sequence data over time, thereby identifying the subject as having a neoplasia or monitoring disease status of the subject.

10. The method of claim 9, wherein an increase in chromosomal copy number alterations between a first time point and a later time point indicates that the subject's disease state has progressed or wherein a decrease in chromosomal copy number alterations between a first time point and a later time point indicates that the subject's disease state has stabilized or is not progressing.

11. A method of characterizing the efficacy of treatment of a subject having a disease characterized by an increase in chromosomal copy number, the method comprising:
(a) isolating fragments of cell-free DNA from two or more biological samples derived from a subject undergoing cancer therapy, wherein a first biological sample is obtained at a first time point and a second or subsequent biological sample is obtained at a later time point;
(b) constructing two or more unamplified, cell-free DNA libraries each comprising fragments from said samples, wherein each library is constructed using from about 2 ng to about 85 ng of DNA;
(c) obtaining sequence data for each library by sequencing the libraries to at least about 0.01-5× genome- or exome-wide sequencing coverage;
(d) generating a copy number alteration profiles from the sequence data, and
(e) using the copy number alteration profiles to compare focal chromosomal copy number alterations in the sequence data over time, thereby characterizing the efficacy of treatment.

12. The method of claim 11, wherein a decrease in chromosomal copy number alterations between the first and later time points indicates that the treatment is effective.

13. The method of claim 11, wherein the disease is cancer.

14. The method of claim 12, wherein the treatment is an anti-cancer therapy selected from the group consisting of chemotherapy, radiotherapy, or surgery.

15. The method of claim 1, wherein the fragments of DNA are cell-free DNA.

16. The method of claim 1, wherein the exome-wide or genome-wide sequencing coverage is about 0.1×.

17. The method of claim 2, wherein detection of a focal chromosomal copy number alteration in the sequence data identifies the presence of tumor derived cell-free DNA present in the sample or wherein failure to detect a focal chromosomal copy number alteration in the sequence data indicates the absence of tumor derived cell-free DNA present in the sample.

18. The method of claim 2, wherein the focal chromosomal copy number alteration correlates with at least about 3% purity of tumor derived DNA.

19. The method of claim 1, wherein the library is constructed using about 5 ng of DNA.

20. The method of claim 1, wherein about 1% of the library is sequenced in (c).

* * * * *